US006613955B1

(12) United States Patent
Lindsay et al.

(10) Patent No.: US 6,613,955 B1
(45) Date of Patent: Sep. 2, 2003

(54) ABSORBENT ARTICLES WITH WICKING BARRIER CUFFS

(75) Inventors: Jeffrey Dean Lindsay, Appleton, WI (US); Fung-jou Chen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/411,260

(22) Filed: Oct. 1, 1999

(51) Int. Cl.[7] ............................................. A61F 13/15
(52) U.S. Cl. ................. 604/378; 604/379; 604/385.28
(58) Field of Search ............................. 604/378, 379, 604/385.01, 385.28, 385.101, 385.17

(56) References Cited

U.S. PATENT DOCUMENTS

| | | | |
|---|---|---|---|
| 2,064,431 A | 12/1936 | Jurgensen | |
| 2,683,457 A | 7/1954 | Cunningham | |
| 2,721,554 A | * 10/1955 | Joa ........................... | 128/290 |
| 2,747,575 A | 5/1956 | Mercer | |
| 3,126,888 A | 3/1964 | Woldman | |
| 3,156,242 A | 11/1964 | Crowe, Jr. | |
| 3,294,091 A | 12/1966 | Morse | |
| 3,575,174 A | 4/1971 | Mogor | |
| 3,667,466 A | 6/1972 | Ralph | |
| 3,860,003 A | 1/1975 | Buell | |

(List continued on next page.)

FOREIGN PATENT DOCUMENTS

| | | | |
|---|---|---|---|
| AU | 699325 | 12/1998 | |
| CA | 884608 | 11/1971 | |
| DE | 196 40 451 A1 | 4/1998 | |
| EP | 0136524 A1 | 4/1985 | |
| EP | 0360285 A2 | 3/1990 | |
| EP | 0360285 | * 3/1990 | ............ A61F/13/15 |
| EP | 0 400 895 A1 | 12/1990 | |
| EP | 0520884 A1 | 12/1992 | |
| EP | 0 117 613 B2 | 3/1993 | |
| EP | 0 564 307 A1 | 10/1993 | |

(List continued on next page.)

OTHER PUBLICATIONS

AATCC Test Method 127–1977, "Water Resistance: Hydrostatic Pressure Test," Technical Manual of the American Association of Textile Chemists and Colorists, reaffirmed 1977, p. 242.

American Society for Testing Materials (ASTM) Designation: D 3574–91, "Standard Test Methods for Flexible Cellular Materials—Slab, Bonded, and Molded Urethane Foams," pp. 303–319, published Mar. 1992.

American Society for Testing Materials (ASTM) Designation: D 4032–82, "Standard Test Method for Stiffness of Fabric by the Circular Bend Procedure," pp. 702–706, published Aug. 1982.

(List continued on next page.)

*Primary Examiner*—Weilun Lo
*Assistant Examiner*—Jacqueline Stephens
(74) *Attorney, Agent, or Firm*—Pauley Petersen Kinne & Erickson

(57) ABSTRACT

An absorbent article is disclosed comprising a thin, flexible wicking barrier with a horizontal portion that is folded back upon itself to create a substantially longitudinal cuff. The wicking barrier can separate a central absorbent member from an outer absorbent member for improved center fill, with the cuff open toward the central absorbent member to intercept liquid flowing toward the longitudinal sides of the article. The wicking barrier cuff desirably contains spacer means to hold the cuff open, providing void space to receive fluid. In one embodiment, lateral compression of the article during use causes the wicking barrier cuff to lift up from the surface of the article, creating a bubble of topsheet material and wicking barrier material (a "dynamic bubble cuff") that intercepts fluid and improves body fit and leakage prevention.

54 Claims, 7 Drawing Sheets

U.S. PATENT DOCUMENTS

| | | |
|---|---|---|
| 3,881,489 A | 5/1975 | Hartwell |
| 3,881,491 A | 5/1975 | Whyte |
| 3,921,232 A | 11/1975 | Whyte |
| 3,989,867 A | 11/1976 | Sisson |
| 4,015,604 A | 4/1977 | Csillag |
| 4,100,324 A | 7/1978 | Anderson et al. |
| 4,195,634 A | 4/1980 | DiSalvo et al. |
| 4,247,362 A | 1/1981 | Williams |
| 4,285,343 A | 8/1981 | McNair |
| 4,324,246 A | 4/1982 | Mullane et al. |
| 4,342,314 A | 8/1982 | Radel et al. |
| 4,397,644 A | 8/1983 | Matthews et al. |
| 4,405,326 A | 9/1983 | Lenaghan |
| 4,421,812 A | 12/1983 | Plant |
| 4,425,130 A | 1/1984 | DesMarais |
| 4,463,045 A | 7/1984 | Ahr et al. |
| 4,476,180 A | 10/1984 | Wnuk |
| 4,480,516 A | 11/1984 | Leroy |
| 4,490,147 A | 12/1984 | Pierce et al. |
| 4,496,359 A | 1/1985 | Pigneul |
| 4,536,181 A | 8/1985 | Cook |
| 4,556,146 A | 12/1985 | Swanson et al. |
| 4,556,560 A | 12/1985 | Buckingham |
| 4,573,986 A | 3/1986 | Minetola et al. |
| 4,576,596 A | 3/1986 | Jackson et al. |
| 4,576,597 A | 3/1986 | Hlaban et al. |
| 4,578,070 A | 3/1986 | Holtman |
| 4,589,876 A | 5/1986 | Van Tilburg |
| 4,608,047 A | 8/1986 | Mattingly |
| 4,654,040 A | 3/1987 | Luceri |
| 4,655,759 A | 4/1987 | Romans-Hess et al. |
| 4,662,876 A | 5/1987 | Wiegner |
| 4,687,478 A | 8/1987 | Van Tilburg |
| 4,695,278 A * | 9/1987 | Lawson ..................... 604/385 |
| 4,701,177 A | 10/1987 | Ellis et al. |
| RE32,649 E | 4/1988 | Brandt et al. |
| 4,738,677 A | 4/1988 | Foreman |
| 4,753,644 A | 6/1988 | Cottenden et al. |
| 4,758,240 A | 7/1988 | Glassman |
| 4,804,380 A | 2/1989 | Lassen et al. |
| 4,846,824 A | 7/1989 | Lassen et al. |
| 4,879,170 A | 11/1989 | Radwanski et al. |
| 4,886,513 A | 12/1989 | Mason, Jr. et al. |
| 4,936,839 A | 6/1990 | Molee et al. |
| 4,950,264 A | 8/1990 | Osborn, III |
| 4,961,736 A | 10/1990 | McCloud |
| 4,964,857 A | 10/1990 | Osborn |
| 4,973,325 A | 11/1990 | Sherrod et al. |
| 5,007,906 A | 4/1991 | Osborn, III et al. |
| 5,009,653 A | 4/1991 | Osborn, III |
| 5,030,314 A | 7/1991 | Lang |
| 5,147,343 A | 9/1992 | Kellenberger |
| 5,147,345 A | 9/1992 | Young et al. |
| 5,151,092 A | 9/1992 | Buell et al. |
| 5,188,625 A | 2/1993 | Van Iten et al. |
| 5,217,445 A | 6/1993 | Young et al. |
| 5,217,447 A | 6/1993 | Gagnon |
| 5,219,342 A | 6/1993 | Hatch et al. |
| 5,235,515 A | 8/1993 | Ungpiyakul et al. |
| 5,236,428 A | 8/1993 | Zajaczkowski |
| 5,267,992 A | 12/1993 | Van Tilburg |
| 5,300,055 A | 4/1994 | Buell |
| 5,308,346 A | 5/1994 | Sneller et al. |
| 5,324,278 A | 6/1994 | Visscher et al. |
| 5,324,575 A | 6/1994 | Sultze et al. |
| 5,342,337 A | 8/1994 | Runeman et al. |
| 5,342,342 A | 8/1994 | Kitaoka |
| 5,350,624 A | 9/1994 | Georger et al. |
| 5,354,400 A | 10/1994 | Lavash et al. |
| 5,360,420 A | 11/1994 | Cook et al. |
| 5,389,094 A | 2/1995 | Lavash et al. |
| 5,399,175 A | 3/1995 | Glaug et al. |
| 5,399,412 A | 3/1995 | Sudall et al. |
| 5,401,267 A | 3/1995 | Couture-Dorschner et al. |
| 5,413,568 A | 5/1995 | Roach et al. |
| 5,415,643 A | 5/1995 | Kolb |
| 5,429,628 A | 7/1995 | Trinh et al. |
| 5,429,629 A | 7/1995 | Latimer et al. |
| 5,429,630 A | 7/1995 | Beal et al. |
| 5,445,628 A | 8/1995 | Gipson et al. |
| 5,447,507 A | 9/1995 | Yamamoto |
| 5,462,166 A | 10/1995 | Minton et al. |
| 5,476,457 A | 12/1995 | Roessler et al. |
| 5,487,736 A | 1/1996 | Van Phan |
| 5,489,283 A | 2/1996 | Van Tillburg |
| 5,506,035 A | 4/1996 | Van Phan et al. |
| 5,514,104 A | 5/1996 | Cole et al. |
| 5,518,801 A | 5/1996 | Chappell et al. |
| 5,520,674 A | 5/1996 | Lavon et al. |
| 5,533,991 A | 7/1996 | Kirby et al. |
| 5,542,941 A | 8/1996 | Morita |
| 5,545,156 A | 8/1996 | DiPalma et al. |
| 5,547,745 A | 8/1996 | Hansen et al. |
| 5,562,645 A | 10/1996 | Tanzer et al. |
| 5,562,650 A | 10/1996 | Everett et al. |
| 5,567,260 A | 10/1996 | McFall |
| 5,575,785 A | 11/1996 | Gryskiewicz et al. |
| 5,591,146 A | 1/1997 | Hasse |
| 5,591,148 A | 1/1997 | McFall et al. |
| 5,591,150 A | 1/1997 | Olsen et al. |
| 5,599,339 A | 2/1997 | Horney |
| 5,601,544 A | 2/1997 | Glaug et al. |
| 5,611,790 A | 3/1997 | Osborn, III et al. |
| 5,618,282 A | 4/1997 | Schlangen |
| 5,620,430 A | 4/1997 | Bamber |
| 5,624,423 A | 4/1997 | Anjur et al. |
| 5,649,917 A | 7/1997 | Roberts et al. |
| 5,672,248 A | 9/1997 | Wendt et al. |
| 5,692,939 A | 12/1997 | DesMarais |
| 5,693,411 A | 12/1997 | Hansen et al. |
| 5,702,378 A | 12/1997 | Widlund et al. |
| 5,704,928 A | 1/1998 | Morita et al. |
| 5,704,930 A | 1/1998 | Lavash et al. |
| 5,704,932 A | 1/1998 | Hibbard |
| 5,711,970 A | 1/1998 | Lau et al. |
| 5,720,738 A | 2/1998 | Clark |
| 5,725,821 A | 3/1998 | Gannon et al. |
| 5,746,729 A | 5/1998 | Wada et al. |
| 5,753,343 A | 5/1998 | Braun et al. |
| 5,766,213 A | 6/1998 | Hackman et al. |
| 5,769,834 A | 6/1998 | Reiter et al. |
| 5,772,967 A | 6/1998 | Wannlund et al. |
| 5,773,120 A | 6/1998 | Deka et al. |
| 5,779,860 A | 7/1998 | Hollenberg et al. |
| 5,795,921 A | 8/1998 | Dyer et al. |
| 5,800,417 A | 9/1998 | Goerg-Wood et al. |
| 5,817,079 A | 10/1998 | Bergquist et al. |
| 5,817,081 A | 10/1998 | LaVon et al. |
| 5,817,394 A | 10/1998 | Alikhan et al. |
| 5,820,616 A | 10/1998 | Horney |
| 5,824,004 A | 10/1998 | Osborn, III et al. |
| 5,830,202 A * | 11/1998 | Bogdanski et al. ......... 604/378 |
| 5,846,230 A | 12/1998 | Osborn, III et al. |
| 5,851,648 A | 12/1998 | Stone et al. |
| 5,853,867 A | 12/1998 | Harada et al. |
| 5,858,011 A | 1/1999 | Brown et al. |
| 5,858,021 A | 1/1999 | Sun et al. |
| 5,865,824 A | 2/1999 | Chen et al. |
| 5,869,033 A | 2/1999 | Schulz |
| 5,874,070 A | 2/1999 | Trinh et al. |
| 5,874,071 A | 2/1999 | Yu et al. |

| | | | |
|---|---|---|---|
| 5,876,393 A | 3/1999 | Ahr et al. | |
| 5,910,137 A | 6/1999 | Clark et al. | |
| 5,954,705 A * | 9/1999 | Sawaki et al. | 604/385.1 |
| 5,957,906 A | 9/1999 | Roe et al. | |
| 5,957,909 A | 9/1999 | Hammons et al. | |
| 5,990,377 A | 11/1999 | Chen et al. | |
| 6,156,020 A * | 12/2000 | Roe et al. | 604/385.01 |
| 6,191,340 B1 * | 2/2001 | Carlucci et al. | 604/369 |

FOREIGN PATENT DOCUMENTS

| | | | |
|---|---|---|---|
| EP | 0687453 A1 | 12/1995 | |
| EP | 0 612 233 B1 | 4/1996 | |
| EP | 0 552 345 B1 | 9/1996 | |
| EP | 0 516 964 B1 | 11/1996 | |
| EP | 0758543 A1 | 2/1997 | |
| EP | 0768070 A1 | 4/1997 | |
| EP | 0 638 303 B1 | 11/1997 | |
| EP | 0804914 A1 | 11/1997 | |
| EP | 0815817 A1 | 1/1998 | |
| EP | 0 652 736 B1 | 10/1998 | |
| EP | 0868894 A1 | 10/1998 | |
| EP | 0 419 434 B2 | 11/1998 | |
| EP | 0 758 220 B1 | 12/1998 | |
| EP | 0 893 517 A2 | 1/1999 | |
| EP | 0945110 A2 | 9/1999 | |
| GB | 2168612 A | 6/1986 | |
| GB | 2233235 A * | 1/1991 | A61F/13/15 |
| GB | 2306333 A | 5/1997 | |
| WO | WO 83/03051 A1 | 9/1983 | |
| WO | WO 92/07535 A1 | 5/1992 | |
| WO | WO 93/21879 A1 | 11/1993 | |
| WO | WO 94/24973 A1 | 11/1994 | |
| WO | WO 95/24878 A1 | 9/1995 | |
| WO | WO 97/19808 A1 | 6/1997 | |
| WO | WO 97/24283 A1 | 7/1997 | |
| WO | WO 98/22059 A1 | 5/1998 | |
| WO | WO 98/24391 A2 | 6/1998 | |
| WO | WO 98/43684 A1 | 10/1998 | |
| WO | WO 99/00093 A1 | 1/1999 | |
| WO | WO 99/12502 A1 | 3/1999 | |
| WO | WO 00/19955 A2 | 4/2000 | |
| WO | WO 00/19956 A1 | 4/2000 | |
| ZA | 98/4033 | 5/1998 | |

OTHER PUBLICATIONS

Federal Specification UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

Gibson, P.W. et al., "Electrospun Fiber Mats: Transport Properties," AIChE Journal, vol. 45, No. 1, Jan. 1999, pp. 190–195.

Kim, S.H. et al., "Synthesis and Characterization of Dextran–Based Hydrogel Prepared by Photocrosslinking," Carbohydrate Polymers, vol. 40, No. 3, Sep. 1999, pp. 183–190.

Krema, Radko et al., "What's New In Highloft Production?" Nonwovens Industry, Oct. 1997, pp. 74–78.

Lee, Seungsin et al., "Antimicrobial and Blood Repellent Finishes for Cotton and Nonwoven Fabrics Based on Chitosan and Fluoropolymers," Textile Research Journal, 69(2)Feb. 1999, pp. 104–112.

Rahn, K. et al., "New Cellulosic Polymers By Subsequent Modification of 2,3–Dialdehyde Cellulose," Cellulose Chemistry and Technology, 32, 1998, pp. 173–183.

* cited by examiner

ABSORBENT ARTICLES WITH WICKING BARRIER CUFFS

BACKGROUND OF THE INVENTION

To prevent leakage of body exudates from absorbent articles such as feminine care pads or napkins and disposable diapers, it is desirable that the exudates not reach the edges of the absorbent material in the article. A "center fill" strategy is desirable for leakage control, wherein fluids are preferentially held in a central region of the article. Unfortunately, in traditional absorbent articles, there is generally no barrier to bulk flow or capillary wicking from the target region to the edges of the article, so leaking from the edges of the article is a persistent problem. Thus, in traditional articles, fluid entering the center of the article still has the potential to travel to the sides and leak. Flow from the center to the sides can be especially rapid when the article is compressed, bringing the wet central portion of the article in contact with absorbent material at the sides of the article.

A variety of wicking barriers have been proposed, including barriers between absorbent components of an absorbent core. However, such wicking barriers generally serve a negative purpose only, that of hindering wicking and lack means for directly channeling flow. What is needed are flow barriers in an absorbent article that not only obstruct flow but provide void volume for receiving flow and means for directing flow to available absorbent material. Ideally, such barriers should also promote effective center fill performance of the absorbent article and efficient use of the absorbent materials of the absorbent core, while also functioning to improve body fit.

SUMMARY OF THE INVENTION

In an absorbent article comprising a central absorbent member separated from the rest of the absorbent core by a flexible wicking barrier such as a polymeric film that hinders flow from the central absorbent member to the longitudinal sides of the article, it has been discovered that the wicking barrier can be modified to define cuffs that intercept and receive fluid. The cuffs can extend longitudinally or in other directions to form flow channels capable of directing fluid to desired destinations in the absorbent core. These benefits can be achieved when the wicking barrier reverses direction (e.g., is folded back upon itself) with opposing edges of the wicking barrier being closer to each other than are the outer portions of the wicking barrier where the reversal or folding occurs.

Desirably, the cuffs extend in a substantially longitudinal direction with the loci of folding occurring in the longitudinal direction, with the longitudinal edges of the wicking barrier reversing back toward the longitudinal centerline of the article. Thus, a transverse cross-section of an absorbent article with substantially longitudinal wicking barrier cuffs can show that the wicking barrier extends laterally outward from the sides of the central absorbent member toward the longitudinal sides of article but then reverses direction such that the edges of the wicking barrier are disposed laterally inward from the laterally outermost portions of the wicking barrier. Spacer means can also be provided to hold the cuff open, providing void space between the upper and lower portions of the folded-over wicking barrier, with the void space being accessible to fluid flowing from the center of the absorbent article toward the longitudinal sides thereof.

Hence, in one aspect, the invention resides in an absorbent article for use on the body of a wearer, the absorbent article having two longitudinal sides, a target zone and a body side, the absorbent article comprising:
 a) a liquid impervious backsheet;
 b) a liquid pervious topsheet attached to the backsheet;
 c) an absorbent core positioned between the topsheet and the backsheet, the absorbent core comprising an outer absorbent member and a central absorbent member, the outer absorbent member having a width in the target zone greater than the width of the central absorbent member in the target zone; and
 d) a wicking barrier spanning a vertical distance between the outer absorbent member and the central absorbent member, further comprising a folded-over portion above the absorbent core forming a wicking barrier cuff open toward the central absorbent member, the wicking barrier cuff further comprising optional spacer means to hold the cuff open to receive fluid.

In another aspect, the invention resides in an absorbent article having a longitudinal direction, a transverse direction, a vertical direction substantially normal to both the longitudinal and transverse directions, and a body side, comprising:
 a) a fluid pervious topsheet on the body side of the article;
 b) a backsheet connected to the topsheet;
 c) an absorbent core having a body side surface, the core being disposed between the backsheet and the topsheet, the core comprising an outer absorbent member having a central void open toward the body side of the article, and a central absorbent member disposed over the central void of the outer absorbent member and extending into the void; and
 d) a wicking barrier disposed between the outer absorbent member and the central absorbent member, the wicking barrier comprising a vertical component between the outer absorbent member and the central absorbent member and a wicking barrier cuff on the body side surface of the absorbent core.

The central void can be a hole that passes completely through the outer absorbent member, or can be a depressed region within a contiguous, uninterrupted outer absorbent member. In one embodiment, the central void longitudinally divides the outer absorbent member into two discontiguous sections. In other embodiments, the outer absorbent member is divided by the central void in the crotch region, but the outer absorbent member may be contiguous in the front or back portions of the article (i.e., the central void does not extend substantially beyond the crotch region).

In another aspect, the invention resides in an absorbent article for use on the body of a wearer, the absorbent article having two longitudinal sides, a target zone and a body side, the absorbent article comprising:
 a) a liquid impervious backsheet;
 b) a liquid pervious topsheet attached to the backsheet;
 c) an absorbent core positioned between the topsheet and the backsheet, the absorbent core comprising a central portion and an outer portion; and
 d) a wicking barrier spanning a vertical distance between the outer portion and the central portion, further extending laterally outward from the central portion toward a longitudinal side of the article to span a first horizontal distance, whereupon the wicking barrier folds back upon itself toward the longitudinal centerline, spanning a second horizontal distance and forming a wicking barrier cuff with an upper layer and a lower layer, the cuff being open toward the central absorbent member and closed toward the longitudinal sides of the article.

In another aspect, the invention resides in an absorbent article for use on the body of a wearer, the absorbent article having two longitudinal sides, a longitudinal centerline, a target zone and a body side, the absorbent article comprising:

a) a backsheet;
b) a liquid pervious topsheet attached to the backsheet;
c) a central absorbent member positioned between the topsheet and the backsheet, the central absorbent member comprising longitudinal sides and a body-side surface;
d) a wicking barrier that extends beneath the central absorbent member, wraps the longitudinal sides thereof, and thereupon extends a horizontal distance on the body-side surface thereof toward the longitudinal centerline of the absorbent article; and
e) spacer means to provide void space between the central absorbent member and the portion of the wicking barrier above the body-side surface of the central absorbent member, thereby forming a wicking barrier cuff.

In another aspect, the invention resides in an absorbent article for use on the body of a wearer, the absorbent article having two longitudinal sides, a target zone, a body side, and a longitudinal centerline, the absorbent article comprising:

a) a backsheet;
b) a liquid pervious topsheet attached to the backsheet;
c) an absorbent core positioned between the topsheet and the backsheet, the absorbent core comprising longitudinal sides, a body-side surface, a lower absorbent layer having a width, and an upper absorbent layer having a width substantially less than the width of the lower absorbent layer; and
d) a substantially impervious wicking barrier extending along a portion of the body-side surface of the lower absorbent layer in the target region and further being folded about a substantially longitudinal folding line toward the longitudinal centerline of the absorbent article to form a wicking barrier cuff having an upper layer and a lower layer, the upper layer being attached to the topsheet, and the folding line being transversely away from the upper absorbent layer.

In this embodiment, the folding line is transversely away from the upper absorbent layer because there is a finite distance in the transverse direction, normal to the longitudinal direction, such as at least 0.5 mm or about 2 mm, between the folding line and the nearest longitudinal side of the upper absorbent layer. The upper layer of the wicking barrier can contact the body-side surface of the upper absorbent layer of the absorbent core, a geometrical configuration which helps to hold the wicking barrier cuff open to receive fluid. Generally, lateral compression in the target region will cause the portion of the topsheet attached to the upper layer of the wicking barrier cuff to deflect upwards, forming a dynamic bubble cuff capable of receiving fluid flowing transversely outward from the center of the article.

In still another aspect, the invention resides in a method for producing an absorbent article having a longitudinal centerline, the method comprising:

a) preparing a lower layer of absorbent material having a width;
b) disposing a wicking barrier over the lower layer of absorbent material, the wicking barrier having a width substantially greater than the width of the lower layer of absorbent material;
c) disposing an upper absorbent layer over the wicking barrier, the upper absorbent layer having a width less than the width of the outer absorbent member;
d) folding the transversely outer portions of the wicking barrier back toward the longitudinal centerline of the article to form wicking barrier cuffs each comprising a lower layer and an upper layer, the upper layer having a free end toward the longitudinal centerline of the article;
e) disposing a backsheet beneath the lower layer of absorbent material; and
f) disposing a topsheet over the article and attaching the topsheet to the backsheet.

The lower absorbent layer may further comprise a central void or depression into which the upper absorbent layer or an absorbent pledget will fit.

In yet another aspect, the invention resides in a method for producing an absorbent article having a central absorbent member, a garment side, a body side, and a longitudinal centerline, the method comprising:

a) providing a central strip of absorbent material and two side strips of absorbent material to form an incipient absorbent core;
b) placing a thin, flexible wicking barrier below the central strip and above the two side strips, the wicking barrier having a width substantial greater than the width of the central strip;
c) upwardly folding the transversely outer portions of the wicking barrier back upon themselves and toward the longitudinal centerline of the central strip to form wicking barrier cuffs;
d) disposing a backsheet beneath the central strip and two side strips, the backsheet having larger in-plane dimensions that the combined central strip and two side strips; and
e) disposing a topsheet over the central absorbent strip and two side strips, wherein the topsheet is further connected to the backsheet at the outer periphery thereof.

The above method may further comprise inserting or providing spacer means in the wicking barrier cuff and/or adhesively attaching the topsheet to the body-side surface (i.e., the upper layer) of the wicking barrier cuffs.

Generally, absorbent articles according to the present invention comprise a topsheet attached to a backsheet with an absorbent core and a wicking barrier therebetween. The absorbent core comprises a central absorbent member that is desirably surrounded by a wider outer absorbent member, with a wicking barrier disposed along at least a portion of the sides of the central absorbent member to hinder fluid flow from the central absorbent member to the sides of the article. The topsheet is liquid pervious to permit intake of fluid and can be any material known in the art such as a spunbond web or apertured film. The backsheet is generally liquid impervious and can be a polyolefin film, for example. The central absorbent member and outer absorbent member or other absorbent components can comprise any known absorbent material known to be useful in absorbent articles, such as cellulosic airlaid webs, fluff pulp, tissue layers, coform, peat moss, and the like. In those embodiments of the present invention having a separate outer absorbent member and a central absorbent member with a wicking barrier therebetween, the central absorbent member generally is the primary absorbent component of the article. The outer absorbent member typically serves as a frame or shaping element for the absorbent article, in part by virtue of its ability to remain dry and resilient in use, but also offers additional absorbent capacity for fluid retention. The outer absorbent member is generally wider and also can be longer than the central absorbent member, and preferably has a central void for receiving at least a portion of the central absorbent member. Alternatively, the outer absorbent member can be a lower layer wider than a narrower upper layer serving as the central absorbent member, with the wicking barrier separating the upper layer from the lower layer and forming at least one and preferably two cuffs to intercept fluid escaping from the upper layer.

The wicking barrier can be any thin, flexible material capable of preventing or hindering flow away from the central absorbent member, with impervious polymeric films such as polyethylene or polypropylene being especially preferred. In a preferred embodiment, the wicking barrier spans a vertical distance between the central absorbent member and an outer absorbent member, and further spans a horizontal distance above the body-side surface of the outer absorbent member. The cuffs formed from a folded portion of the wicking barrier above the absorbent core not only help prevent fluid from reaching the longitudinal sides of the absorbent article, but also can help channel fluid to underutilized portions of the absorbent core for improved absorption. Due to the horizontal component on the surface of the absorbent core, the wicking barrier also serves to prevent fluid communication between the central absorbent member and the outer absorbent member when the article is laterally compressed or bunched together in use. The wicking barrier can also help control the geometry of the absorbent article when in use under dynamic conditions, permitting flexure or folding such that the central region of the core (e.g., the central absorbent member where applicable) is deflected toward the body.

Spacer means to hold the wicking barrier cuffs open can include any of the following or combinations thereof or their equivalents:

1. Attachment of an upper portion of the folded wicking barrier to a structure at a substantially higher elevation than the lower portion of the folded wicking barrier. For example, an upper portion of the wicking barrier may be attached to an elevated central absorbent member which rises above the plane of the outer absorbent member, or may be attached to a portion of the topsheet which in turn is held above the plane of the outer absorbent member by virtue of an elevated central absorbent member.

2. Spacers of absorbent material or non-absorbent material to keep the two layers of barrier material apart. The use of materials which expand in the z-direction when wet can be especially useful for good performance of the article in use.

3. Corrugations, wrinkles, embossments, ribs, or other three-dimensional elements in or on the wicking barrier. For example, thermal embossing of the longitudinal sides of the wicking barrier can yield a sinusoidal or corrugated effect along the edges, similar to the edges of a scallop shell, resulting in open voids directed toward the longitudinal centerline of the absorbent article. The scalloped voids permit fluid flow into the cuff.

A wicking barrier with a scalloped, three-dimensional edge provides elevated portions of the wicking barrier edge lying above the absorbent core and providing void volume for intercepting lateral flow of fluid along the surface of the absorbent core. Similar effects can be achieved with other spacer means described above.

Particularly beneficial improvements in leakage control can be achieved through the interaction between the topsheet and the folded-over portion of the wicking barrier on the surface of the absorbent core, wherein lateral compression of the absorbent article causes a loop or "bubble" of topsheet material to rise along the sides of the article, the loop running substantially in the longitudinal direction, thus helping to provide a "dynamic bubble cuff" that is not present until the article is worn. The dynamic bubble cuff feature is not normally seen in other absorbent articles where the topsheet, such as a nonwoven web, may be adhesively attached over its entire surface to the underlying absorbent core and backsheet. In the present invention, adhesive material joining the topsheet to the upper layer of the folded-over portion of a wicking barrier on the surface of the absorbent core does not directly connect the topsheet to the absorbent core, but connects it to a layer of the wicking barrier that can rise vertically away from the absorbent core. In fact, the upper layer of the folded-over portion of the wicking barrier can move and flex relative to the absorbent core with little resistance from friction, apart from its connection to the lower layer of the folded-over portion along a folding line, provided that any active adhesive on the wicking barrier in the folded-over portion is on the side that contacts the topsheet. The inner surfaces of the wicking barrier which can contact each other should be substantially free of adhesive to prevent the two layer from becoming sealed. Thus, in the present invention, an article may lie flat with little or no indication of a three-dimensional cuff rising vertically away from the plane of the topsheet, but when the article undergoes lateral compression, a bubble with a substantially longitudinal orientation rises away from the absorbent core to act as a barrier for leakage along the surface of the absorbent article and as a means for intercepting and redirecting flow. The bubble, or dynamic bubble cuff, comprises the upper layer of the folded-over portion of the wicking barrier and the portion of the topsheet attached thereto. A dynamic bubble cuff is particularly likely to form when the absorbent core comprises a separate outer absorbent member separated from a central absorbent member by the wicking barrier, as described in pending application Ser. No. 09/165,875, "Absorbent Article with Center Fill Performance," filed Oct. 2, 1998, herein incorporated by reference.

The absorbent core may further comprise a central rising member under the central absorbent member or under or within the absorbent core to translate lateral compression of the core into vertical rising of the central portion of the core for improved body fit. Central rising members and related embodiments are described in commonly owned copending application "Center-fill Absorbent Article with Central Rising Member" by Chen et al., Ser. No. 094/1259, now U.S. Pat. No. 6,492,574 filed the same day as the present application.

Possible uses of the present invention include absorbent articles for intake, distribution, and retention of human body fluids. Likewise, the present invention can be applied to diapers, disposable training pants, other disposable garments such as incontinence pads, bed pads, medical absorbents and wound dressings. The articles of the present invention provide significant leakage protection, fluid center-fill absorptive performance, and other desirable attributes for absorbent articles.

Definitions

"Absorbency Under Load" (AUL) is a measure of the liquid retention capacity of a material under a mechanical load. It is determined by a test which measures the amount in grams of an aqueous solution, containing 0.9 weight percent sodium chloride, a gram of a material can absorb in 1 hour under an applied load or restraining force of about 2 kPa (0.3 pound per square inch).

The AUL apparatus comprises a Demand Absorbency Tester (DAT) as described in U.S. Pat. No. 5,147,343, issued Sep. 15, 1992 to Kellenberger, herein incorporated by reference, which is similar to a GATS (Gravimetric Absorbency Test System), available from M/K Systems, Danners, Mass.

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). Desirably, the absorbent materials used in the absorbent members of the present invention have an Intrinsic Absorbent Capacity of about 2 or greater, more specifically about 4 or greater, more specifically still about 7 or greater, and more specifically still about 10 or greater, with exemplary ranges of from about 3 to about 30 or from about 4 to about 25 or from about 12 to about 40.

As used herein, "absorbent capacity" refers to the total mass of water that a specified quantity of absorbent material can hold, and is simply the Intrinsic Absorbent Capacity multiplied by the dry mass of the absorbent material. Thus 10 g of material having an Intrinsic Absorbent Capacity of 5 has an absorbent capacity of 50 g (or about 50 ml of fluid).

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity and 23° C.) after conditioning for at least four hours. Samples should be essentially flat and uniform under the area of the contacting platen. Bulk is expressed as volume per mass of fiber in cc/g and density is the inverse, g/cc.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, "Central Elevation" is defined as the height difference between the center of the central absorbent member along the transverse centerline of the article and the average height of the longitudinal sides of the central absorbent member along the transverse centerline of the article at the end of the Vertical Deformation Test hereinafter described. The Central Elevation for absorbent articles of the present invention can be at least about 0.5 cm, specifically at least about 1 cm, and more specifically at least about 1.2 cm and up to about 10 cm, Desirably, an absorbent article of the present invention exhibits an increase in Central Elevation in the crotch region of at least about 20%, and more specifically at least about 50%, relative to the Central Elevation in the crotch region exhibited by an essentially identical absorbent article without a shaping line.

As used herein, the "crotch region" of an absorbent article refers to the generally central region that will be in contact with the crotch of the user, near the lowermost part of the torso, and resides between the front and rear portions of the article. Typically the crotch region contains the transverse centerline of the article and generally spans approximately 7 to 10 cm in the longitudinal direction.

Many articles of the present invention are intended to be worn in the crotch of a wearer, and thus have crotch regions. However, the present invention can also be applied to other articles such as underarm pads or wound dressings where a crotch region may not exist. In such cases, the article will have a region where fluid intake is intended to occur, termed the "target region." The portion of the article including the longitudinal length of the target region and the full transverse width of the article normal to length of the target region is defined herein as the "target zone." For articles intended to be worn in the crotch, the terms "target zone" and "crotch region" are generally synonymous, whereas "target region" generally excludes the portions of the absorbent core near the longitudinal sides since the intended area for fluid intake is generally substantially central in the absorbent article.

As used herein, the term "extensible" refers to articles that can increase in at least one of their dimensions in the x-y plane by at least 10% and desirably at least 20%. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions. Preferably, the article is extensible at least in the longitudinal direction. Examples of extensible materials and articles, and their methods of preparation, are disclosed in U.S. Pat. No. 5,611,790, issued Mar. 18, 1997 to Osborn, herein incorporated by reference in its entirety.

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article desirably has a flexure-resistance of less than or equal to about 1,500 grams, more specifically about 1000 grams or less, more specifically still about 700 grams or less and most specifically about 600 grams or less. For shaping performance, the central absorbent member as well as the outer absorbent member can have a flexure resistance of at least about 30 grams, more specifically at least about 50 grams, and most specifically at least about 150 grams.

As used herein, "Free Swell Capacity" (FS) is the result of a test which measures the amount in grams of an aqueous solution, containing 0.9 weight percent sodium chloride, that a gram of a material can absorb in 1 hour under negligible applied load. The test is done as described above for the AUL test, except that the 100 gm weight used in the AUL test is not placed on the sample.

The Free Swell Capacity of the materials of the present invention can be above 8, more specifically above 10, more specifically above 20, and most specifically above 30 grams/gram.

As used herein, "Free Swell:AUL Ratio" is the ratio of Free Swell Capacity to AUL. It will generally be greater than one. The higher the value, the more sensitive the material is to compressive load, meaning that the sample is less able to maintain its potential pore volume and capillary suction potential under load. Desirably, the materials of the present invention have "Free Swell:AUL Ratio" of about 4 or less, more specifically about 2 or less, more specifically still about 1.5 or less, and more specifically about 1.3 or less, with an exemplary range of from about 1.2 to about 2.5.

As used herein, "high yield pulp fibers" are those papermaking fibers of pulps produced by pulping processes providing a yield of about 65 percent or greater, more specifically about 75 percent or greater, and still more specifically from about 75 to about 95 percent. Yield is the resulting amount of processed fiber expressed as a percentage of the initial wood mass. High yield pulps include bleached chemithermomechanical pulp (BCTMP), chemithermomechanical pulp (CTMP), pressure/pressure thermomechanical pulp (PTMP), thermomechanical pulp (TMP), thermomechanical chemical pulp (TMCP), high yield sulfite pulps, and high yield Kraft pulps, all of which contain fibers having high levels of lignin.

As used herein, the term "horizontal," refers to directions in the plane of the article that are substantially parallel to the body-side surface of the article, or, equivalently, substantially normal to the vertical direction of the article, and comprises the transverse direction and the longitudinal direction of the article, as well as intermediate directions. The orientation of components in an article, unless otherwise specified, is determined as the article lies substantially flat on a horizontal surface.

As used herein, the term "hydrophobic" refers to a material having a contact angle of water in air of at least 90 degrees. In contrast, as used herein, the term "hydrophilic" refers to a material having a contact angle of water in air of less than 90 degrees.

As used herein, "Intrinsic Absorbent Capacity" refers to the amount of water that a saturated sample can hold relative to the dry weight of the sample and is reported as a dimensionless number (mass divided by mass). The test is performed according to Federal Government Specification UU-T-595b. It is made by cutting a 10.16 cm long by 10.16 cm wide (4 inch long by 4 inch wide) test sample, weighing it, and then saturating it with water for three minutes by soaking. The sample is then removed from the water and hung by one corner for 30 seconds to allow excess water to be drained off. The sample is then re-weighed, and the difference between the wet and dry weights is the water pickup of the sample expressed in grams per 10.16 cm long by 10.16 cm wide sample. The Intrinsic Absorbent Capacity value is obtained by dividing the total water pick-up by the dry weight of the sample. If the material lacks adequate integrity when wet to perform the test without sample disintegration, the test method may be modified to provide improved integrity to the sample without substantially modifying its absorbent properties. Specifically, the material may be reinforced with up to 6 lines of hot melt adhesive having a diameter of about 1 mm applied to the outer surface of the article to encircle the material with a water-resistant band. The hot melt should be applied to avoid penetration of the adhesive into the body of the material being tested. The corner on which the sample is hung in particular should be reinforced with external hot melt adhesive to increase integrity if the untreated sample cannot be hung for 30 seconds when wet.

"Papermaking fibers," as used herein, include all known cellulosic fibers or fiber mixes comprising cellulosic fibers. Fibers suitable for making the webs of this invention comprise any natural or synthetic cellulosic fibers including, but not limited to nonwoody fibers, such as cotton, abaca, kenaf, sabai grass, flax, esparto grass, straw, jute hemp, bagasse, milkweed floss fibers, and pineapple leaf fibers; and woody fibers such as those obtained from deciduous and coniferous trees, including softwood fibers, such as northern and southern softwood kraft fibers; hardwood fibers, such as eucalyptus, maple, birch, and aspen. Woody fibers can be prepared in high-yield or low-yield forms and can be pulped in any known method, including kraft, sulfite, high-yield pulping methods, and other known pulping methods. Chemically treated natural cellulosic fibers can be used such as mercerized pulps, chemically stiffened or crosslinked fibers, or sulfonated fibers. Suitable papermaking fibers can also include recycled fibers, virgin fibers, or mixes thereof.

As used herein, a "pledget" refers to an absorbent insert within an absorbent core having at least one of a width and a length smaller than the respective width and length of the absorbent core. A pledget is generally used to cause deformation or shaping of an adjoining layer of an absorbent article, and in the present invention, can be of use in shaping a pad or creating a medial hump in the pad for improved fit against the body of the wearer.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as panty liners, or other absorbent articles such as diapers or incontinence pads. The term "feminine care pad" as used herein is synonymous with sanitary napkin.

The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

As used herein, "thickness" of a fluff pad or other absorbent element refers to thickness measured with a platen-based thickness gauge having a diameter of 7.62 cm at a load of about 0.05 pounds per square inch (psi) [about 35 kilograms per square meter]. The thickness of the central absorbent member or the outer absorbent member or of the absorbent article in general can be from about 2 mm to about 50 mm, more specifically from about 3 mm to about 25 mm, more specifically still from about 3 mm to about 15 mm, and most specifically from about 4 mm to about 10 mm. Ultrathin articles can have a thickness less than about 6 mm.

As used herein, the term "transverse" refers to a line, axis, or direction which lies within the plane of the absorbent article and is generally perpendicular to the longitudinal direction. The z-direction is generally orthogonal to both the longitudinal and transverse centerlines. The term "lateral" refers to substantially in-plane directions having a predominately transverse component. Likewise, "inwardly lateral compression" refers to compression directed from the longitudinal sides of an article toward the longitudinal centerline thereof, applied substantially in the transverse direction.

The degree of elevation of the central absorbent member can be quantified in terms of a Vertical Deformation test. As used herein, "Vertical Deformation" refers to the height increase experienced by the body-side surface of an absorbent article when the longitudinal sides in the crotch reason are gripped and steadily moved inward toward the longitudinal axis of the article, decreasing the span between the longitudinal sides by 1.5 cm. The Vertical Deformation test apparatus comprises two clamps having a clamp width (longitudinal length of the clamped portion of the edge of the article) of 5 cm. One clamp is stationary and the other is on a track that permits the clamp to slide to increase or decrease the distance between the clamps while keeping the clamp aligned and parallel to the other clamp. The clamps should be tilted downward at an angle of 20 degrees relative to horizontal, such that both outer edges of the absorbent article are slightly elevated relative to the nearest crease line, thus somewhat simulating the positioning of the outward edges of the absorbent article that may be induced by panties with elevated elastic edges in the crotch region. The clamps are 5 cm above the surface of the track, permitting a pad to be suspended in air between the clamps, gripped in the crotch area such that a portion of the longitudinal sides of the absorbent core are held, with the clamps extending inward no more than about 3 mm from the outer edge of the absorbent core. The article should be held substantially taut in the region between the clamps without damaging the article, such that the crotch region is substantially horizontal before lateral compression begins. At a rate of about 0.5 centimeters per second (cm/s), the slidable clamp is moved smoothly toward the fixed clamp by a distance of 50% of the initial width of the article in the crotch region (or less if the article become incompressible such that more than about 5 kg of force is required to further compress the article). The height of the center of the pad or absorbent article is recorded before the clamp is moved and after the clamp is moved, yielding a difference that is reported as the Vertical Deformation. An increase in height is reported as a positive number, while a decrease is reported as a negative number. Desirably, the Vertical Deformation of the absorbent article is at least about 0.5 cm. Specifically, the Vertical Deformation is at least about 1 cm, and more specifically is at least about 1.5 cm and up to about 10 cm. Desirably, an absorbent article of the present invention exhibits an increase in Vertical Deformation in the crotch region of at least about 20%, and more specifically at least about 50%, relative to the Vertical Deformation in the crotch region exhibited by an essentially identical absorbent article without a shaping line.

As used herein, "Wet Bulk" is based on a caliper measurement of a sample according to the definition of "bulk" above (at 0.344 kPa), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk in cc/g is calculated as the thickness of the substantially planar moistened sample under a load of 0.344 kPa (0.05 psi) divided by the oven-dry sample basis weight. Absorbent materials in the absorbent members of the present invention can have a Wet Bulk of about 4 cc/g or greater, more specifically about 6 cc/g or greater, more specifically still about 10 cc/g or greater, more specifically still about 10 cc/g or greater, and most specifically about 15 cc/g or greater, with an exemplary range of from about 5 cc/g to about 20 cc/g.

DETAILED DESCRIPTION OF THE DRAWINGS

Figure 1A:
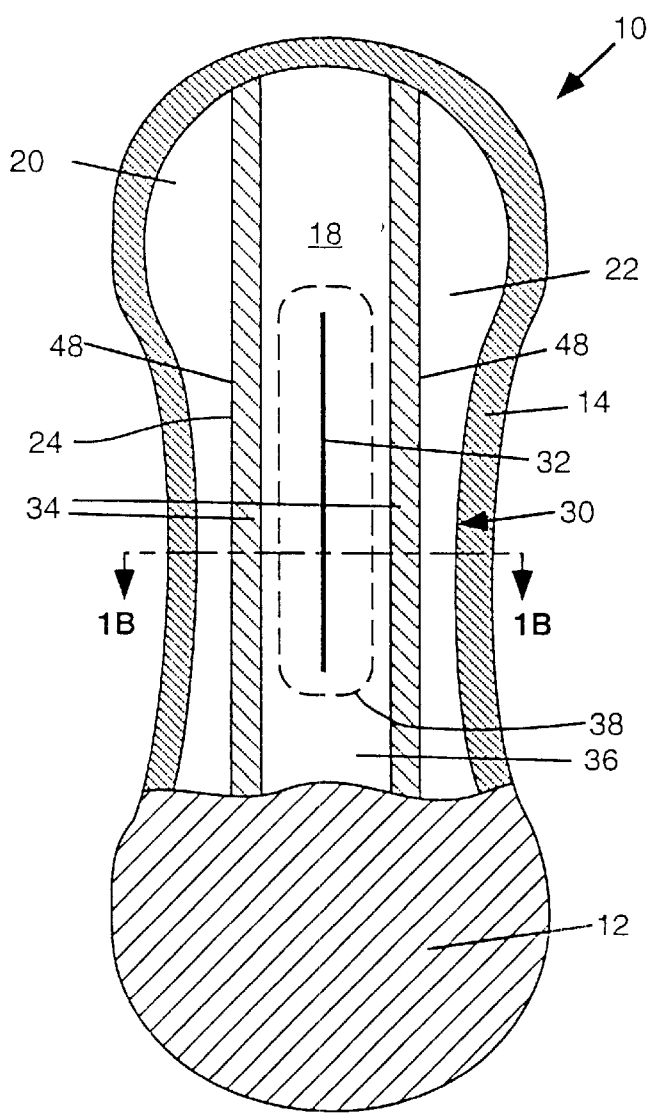
FIGS. 1A and 1B depict a top view and transverse cross-sectional view, respectively, of an absorbent article according to the present invention having a central absorbent member, an outer absorbent member, and a wicking barrier with wicking barrier cuffs.
Figure 1B:
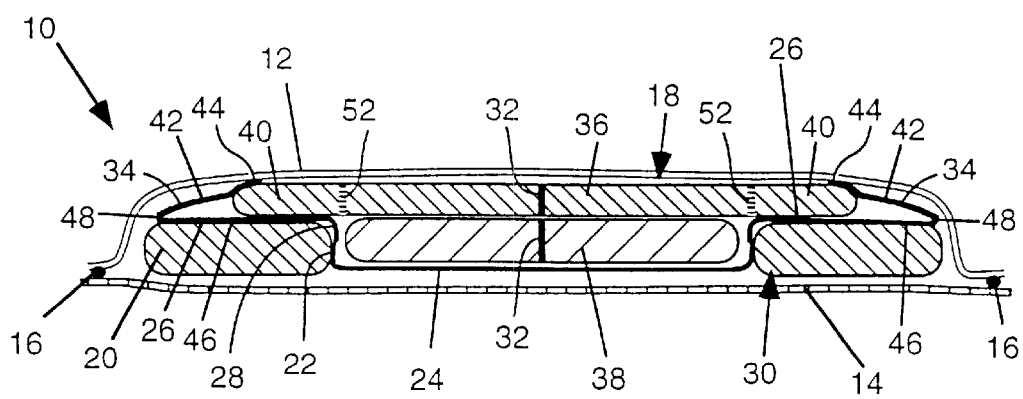

FIGS. 1A and 1B depict a sanitary napkin 10 according to the present invention. FIG. 1A provides a top view, with some elements not visible, while FIG. 1B depicts more detail in a cross-section taken near the longitudinal center of the napkin in the transverse direction. The napkin 10 comprises an absorbent core 30 between a liquid pervious topsheet 12 (cutaway in FIG. 1A to reveal underlying components) and a liquid impervious backsheet 14 joined together with adhesive 16 or other connection means near the longitudinal sides of the article 10. The absorbent core 30 comprises a central absorbent member 18 having an upper absorbent layer 36 and a lower absorbent layer 38, further provided with a longitudinal shaping line 32, which directs the upward folding of the central absorbent member 18 during lateral compression, and with crease lines 52 in the upper absorbent layer 36 to promote downward folding. The central absorbent member 18 is surrounded by an outer absorbent member 20 and resides in a central void 22 defined by the central sides of the outer absorbent member 20. The central absorbent member 18 is separated from the outer absorbent member 20 by a wicking barrier 24. In the embodiment shown, the wicking barrier 24 passes beneath the central absorbent member 18 and has a vertical component 28 extending vertically from beneath the central absorbent member 18 to the surface of the outer absorbent member 20, where it extends horizontally to define a horizontal component 26 or ledge on the surface of the absorbent core 30, and particularly on the surface of the outer absorbent member 20.

The longitudinal sides of the wicking barrier 24 fold back upon themselves over the outer absorbent member 20 to form wicking barrier cuffs 34 which are shown attached to the longitudinal ends 40 of the upper absorbent layer 36 of the central absorbent member 18. The wicking barrier cuffs 34 can also be adhesively attached to the topsheet 12. The wicking barrier cuffs 34 comprise an upper layer 42 having a free end 44 toward the longitudinal centerline of the article 10 and a lower layer 46 which is joined to the upper layer of the cuff 42 at the folding line 48 (in some cases the term "folding region" is more suitable, depending on the suddenness of crispness of the reversal in direction). The wicking barrier cuffs 34 can prevent lateral leakage from the sides of the upper absorbent layer 36, and can direct fluid flow to the longitudinal ends of the absorbent article 10 due to the substantially longitudinal orientation of the cuffs 34.

Generally, when the longitudinal sides of the wicking barrier 24 are folded back upon themselves to make a wicking barrier cuff 34, the body-side surface of the wicking barrier cuff 34 desirably is attached to some elevated component to hold the cuff 34 at least partially open (preventing the over folded layer of wicking barrier material 24 from resting flat upon itself with no void space therebetween), and either the topsheet 12 or an elevated central absorbent member 18 or upper absorbent layer 36 thereof can serve as the elevated component. Other spacer means can be provided as well.

The topsheet 12 is liquid permeable and, when the article 10 is in use, is generally in close proximity to the skin of the user. Desirably, the topsheet 12 is compliant, soft and nonirritating to the user's skin. It can be made from any of the conventional materials for this type of use. Nonlimiting examples of suitable materials include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982. Mechanically apertured forms can also be used. Other known cover materials can be employed, including those made from textured cellulosic basesheets with hydrophobic matter added to selected portions of the basesheet, particularly the most elevated portions of the basesheet, as described in commonly owned U.S. Pat. No. 5,990,377 issued Nov. 23, 1999 "Dual-zoned Absorbent Webs".

Figure 2A:
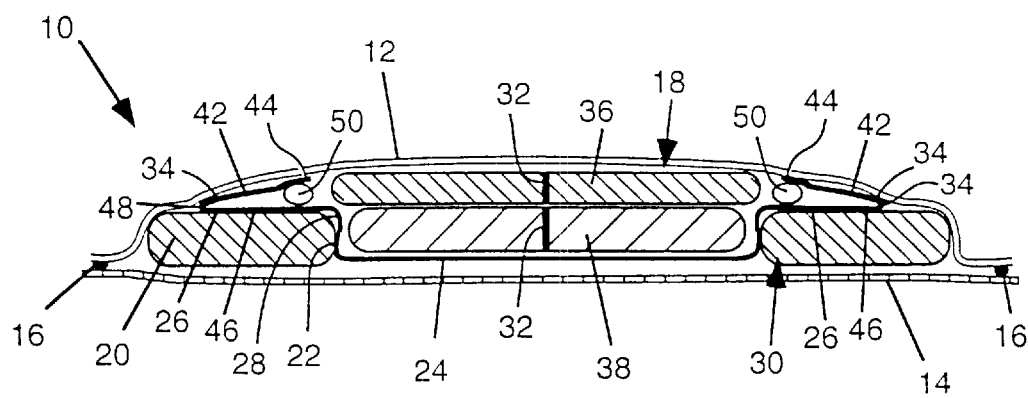
FIGS. 2A and 2B depicts transverse cross-sections of an absorbent article having additional spacer means inserted in the wicking barrier cuff, showing the article before and after lateral compression.
Figure 2B:
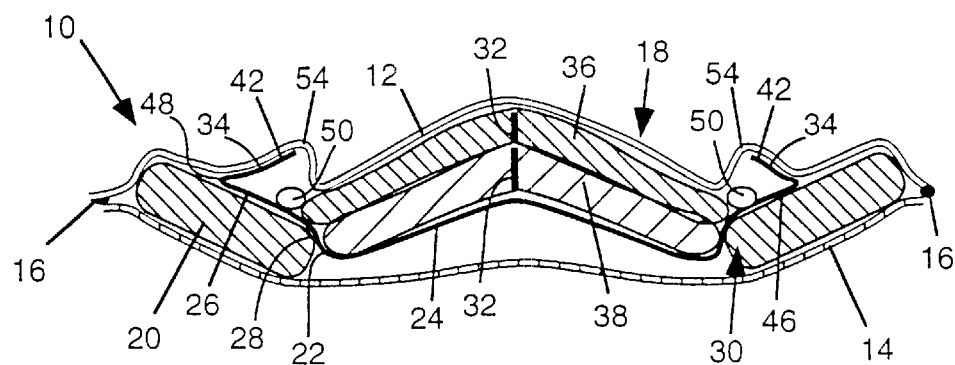

FIGS. 2A and 2B depict cross-sections of a related embodiment, which is shown lying flat in FIG. 2A and shown after lateral compression in FIG. 2B. The upper absorbent layer 36 does not extend so far towards the longitudinal sides of the article 10 as it did in FIG. 1B, and does not contact the free end 44 of the wicking barrier cuff 34. Rather than being attached to the elevated upper absorbent layer 36 of the central absorbent member 18, the upper layer 42 of the wicking barrier cuff 34 is held away from the lower layer 46 thereof by additional spacer means 50, here depicted as spaced apart segments of a compressible material such as foam rubber or other flexible matter spaced longitudinally apart to provide open spaces between the spaced apart spacer means for easy interception of fluid moving toward the longitudinal sides of the article 10. Thus, the spacer means 50 hold open the wicking barrier cuff 34 such that void space is maintained between the two layers 42, 46 for intercepting fluid flowing from the center of the article 10 toward the longitudinal sides thereof.

If the topsheet 12 is provided with adhesive on is garment-side surface, making it adhesively attached to underlying components, the portion of the topsheet 12 between the longitudinal sides of the outer absorbent member 20 and the longitudinal sides of the upper absorbent layer 36 of the central absorbent member 18 will be free to flex away from the absorbent core 30 and toward the body of the wearer when the absorbent article 10 undergoes lateral compression during use. As shown in FIG. 2B, the upward deflection of the longitudinal sides of the outer absorbent member 20 coupled with the lack of direct attachment between the topsheet 12 and the outer absorbent member 20 in the region above the upper layer 42 of the wicking barrier cuff 34 results in formation of a "dynamic bubble cuff" 54, which is a loop or "bubble" of topsheet material connected to the upper layer 42 of the wicking barrier cuff 34. It is termed a "dynamic bubble cuff" 54 because it is an additional cuff-like structure which becomes functional when the article is worn and compressed laterally.

In FIG. 2B, the central absorbent member 18 has buckled toward the body of the user, as desired, and the outer absorbent member 20 is bent to provide an overall W-shape to the cross-section of the article 10. In the embodiment shown, the spacer means 50 (longitudinally spaced apart pieces of a sponge or other resilient material) is not adhesively connected to the upper layer 42 of the wicking barrier cuff 34, permitting it to flex away from the absorbent core 30 to follow the topsheet 12. The dynamic bubble cuff 54 acts as a cuff with increased void space relative to the wicking barrier cuff 34 prior to lateral compression. Further, it acts as a dam or edge cuff rising substantially above the absorbent core to better contact the body and prevent lateral leakage.

The absorbent members in the absorbent core 30 of the article 10 can be any known absorbent material such as a densified airlaid web, a web of fluff pulp, one or more layers of tissue, coform, a hydrophilic foam, open-cell foams, porous fiber-foam composites and the like.

The wicking barrier 24 can comprise any thin, flexible barrier material that reduces lateral wicking of fluid from one absorbent member to another, or from one portion of an absorbent member to another portion. The barrier material can be a polymeric film or plastic film; a hydrophobic nonwoven web; a layer of rubber, silicone, or other non-absorbent materials; or a substantially impervious paper sheet including, for example, glassine, wax paper, impregnated papers, paper-polymer composites, densified tissue, paper or tissue containing internal sizing to render it less hydrophilic, paper or tissue treated with hydrophobic matter such as wax, silicone, thermoplastic material, or polyolefins. Flexible hydrophobic foams may also be used, such as a closed-cell polyurethane foam or a silicone foam. Thin polyolefin films such as polyethylene are preferred because of their impervious nature, their high flexibility, low cost, and ease of handling.

The backsheet 14 is impervious to liquids and, thus, prevents menstrual fluid or other body exudates which may be released from the absorbent core 30 from soiling the body or clothing of the user. Any backsheet material used in the art for such purposes can be utilized herein. Suitable materials are embossed or nonembossed polyethylene films and laminated tissue, desirably treated with sizing agents and wet strength agents. Breathable films that permit moisture transpiration to occur without significant condensation can also be used. The backsheet 14 may be embossed or provided with odor-controlling materials or provided with microencapsulated materials for skin wellness or release of anti-microbial or anti-odor agents upon wetting.

The outer surface of the backsheet 14 can be coated with adhesive such as pressure-sensitive adhesive strips (not shown). The adhesive, for example, can provide a means for securing the pad in the crotch portion of a panty. Any adhesive or glue used in the art for such purposes can be used herein, with pressure sensitive adhesives being preferred. The pressure sensitive adhesive should be covered with one or more removable release liners (not shown). Any commercially available release liners commonly used for such purposes can be utilized.

It is desirable that the width of the central absorbent member 18 be from about 1 to about 12 centimeters, more specifically from about 2 to about 7 centimeters, and most specifically from about 2 to about 5 centimeters.

Figure 3A:
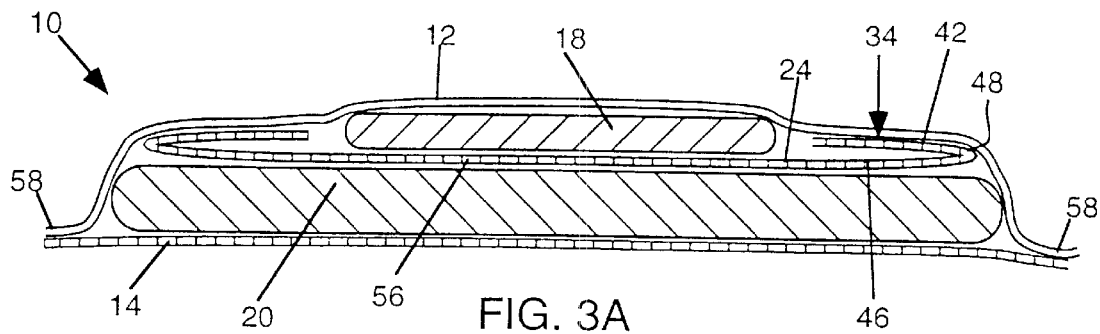
FIGS. 3A to 3C depict forms of absorbent articles having a horizontal wicking barrier with wicking barrier cuffs open toward an upper layer of absorbent material.
Figure 3B:
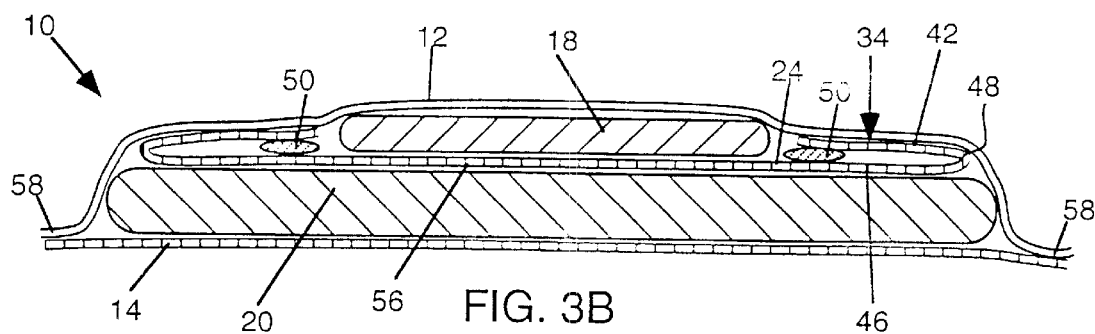

FIGS. 3A to 3B show variations of an absorbent article 10, depicted in a cross-sectional view along the transverse centerline, wherein the wicking barrier 24 does not span a vertical distance between two absorbent members, but separates the central absorbent member 18 (here also an upper absorbent member) from a wider outer absorbent member 20 (here also a lower absorbent member) with a horizontal span 56 beneath the central absorbent member 18. The absorbent core 30 is enclosed between the topsheet 12 and a backsheet 14 which join at the outer perimeter 56. In the embodiment shown in FIG. 3A, the horizontal wicking barrier 24 extends laterally past the longitudinal sides of the central absorbent member 18 to cover a distance along the bodyside surface of the outer absorbent member 20, whereafter it reverses along a folding line 48 (visible only as a point in the cross-sectional view here) to fold back upon itself and toward the longitudinal centerline to define a folded-over portion that serves as a wicking barrier cuff 34 comprising a lower layer 42 and an upper layer 46 joined at the folding line 48. The wicking barrier cuff 34 is open toward the longitudinal centerline of the article. It is held open at least in part by virtue of its attachment to the topsheet 12, which is held slightly away from the plane of the outer absorbent member 20 by the presence of the elevated central absorbent member 18.

FIG. 3B shows additional spacer means 50 in the form of segments of resilient material to hold the upper layer 42 away from the lower layer 46 of the wicking barrier cuff 34. The resilient material desirably should either be highly porous (e.g., porosity over 60%, desirably over 75%, with pores over 100 microns in diameter, and desirably over 150 microns in diameter) or should be spaced discretely in the longitudinal direction such that there are regular openings between the segments of the spacer means 50 to provide open flow pathways for entry of fluid into the wicking barrier cuff 34.

Figure 3C:
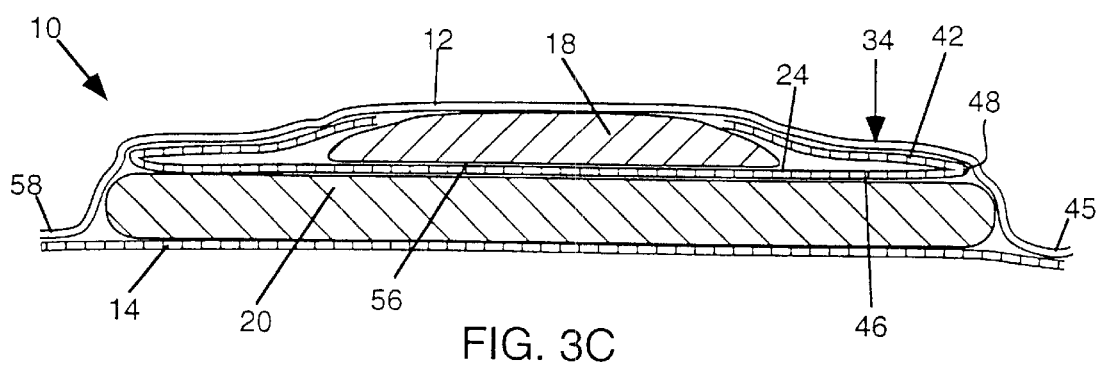

In FIG. 3C, the central absorbent member 18 is tapered and the wicking barrier 24 extends from the folding point 48 sufficiently far to contact the body-side surface of the tapered central absorbent member 18, defining a wicking barrier cuff 34 held open both by contact with the elevated central absorbent member 18 and by contact with the topsheet 12.

Figure 4:
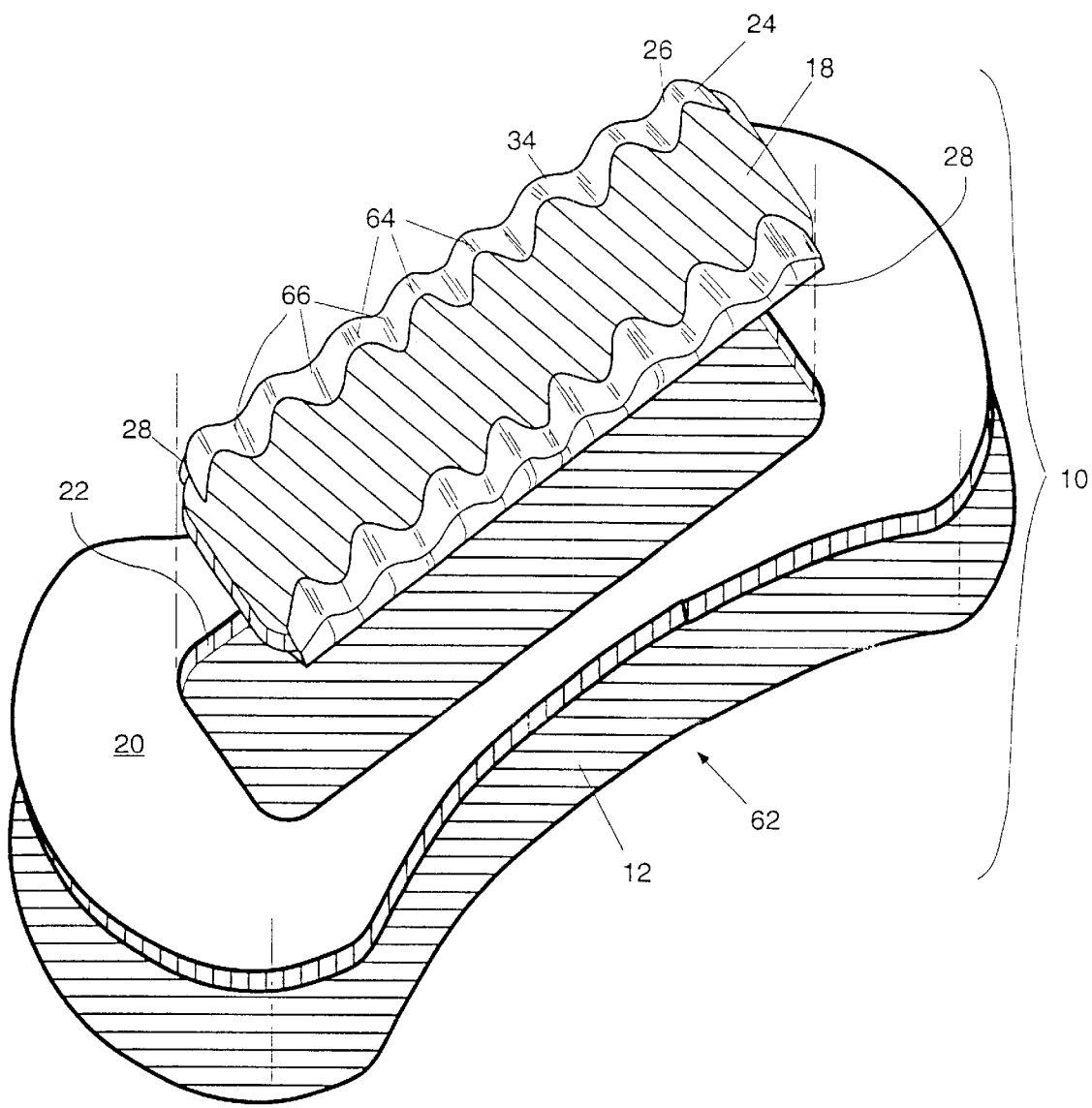
FIG. 4 is an exploded view of an absorbent article having a central absorbent member wrapped with a wicking barrier having a corrugated edge to provide added void volume between the body-side surface of the central absorbent member and wicking barrier.

FIG. 4 depicts an exploded view of an absorbent article 10 comprising an outer absorbent member 20 with a central void 22 therein located substantially in the crotch region 62, a central absorbent member 18 sized to fit within the central void 22, and a thin polymeric wicking barrier 24 that extends below the central absorbent member 20 and wraps the longitudinal sides thereof, defining a vertical component 28 of the wicking barrier 24, and which further extends a distance along the body-side surface of the central absorbent member 18 from the longitudinal sides thereof toward the longitudinal centerline of the article 10, defining an upper horizontal component 26. Thus, the wicking barrier 24 comprises a lower portion (not visible) beneath the central absorbent member 18, vertical components 28 along the longitudinal sides of the central absorbent member 18, and an upper horizontal component 26. The vertical components 28 are also reversal points or folding points where the wicking barrier 24 folds back toward the longitudinal centerline of the article, defining a wicking barrier cuff 34. The wicking barrier 24 would be folded back upon itself were it not for the presence of the sides of the central absorbent member 18 which separate the upper horizontal component 26 of the wicking barrier 24 from the lower portion (not visible) beneath the central absorbent member 18.

The wicking barrier cuff 34 wrapping the edges of the central absorbent member 18 can hinder fluid flowing from the edges of the central absorbent member 18 as well as fluid flowing on or above the body-side surface of the central absorbent member 18. The effectiveness of the wicking barrier cuff 34 in intercepting fluid flowing above the central absorbent member is greatly increased by the presence of spacer means which hold open void spaces above the surface of the central absorbent member 18 capable of receiving fluid flowing laterally outward toward the longitudinal sides of the article 10. The spacer means depicted here comprises vertically scalloped edges of the wicking barrier 24. The vertically scalloped edges are corrugations spanning a distance in the z-direction (vertical direction) such that the upper horizontal component 26 of the wicking barrier cuff 34 comprises a series of elevated regions 64 interspersed with depressed regions 66, the depressed regions contacting the underlying absorbent material (i.e., the central absorbent member 18).

Figure 5:
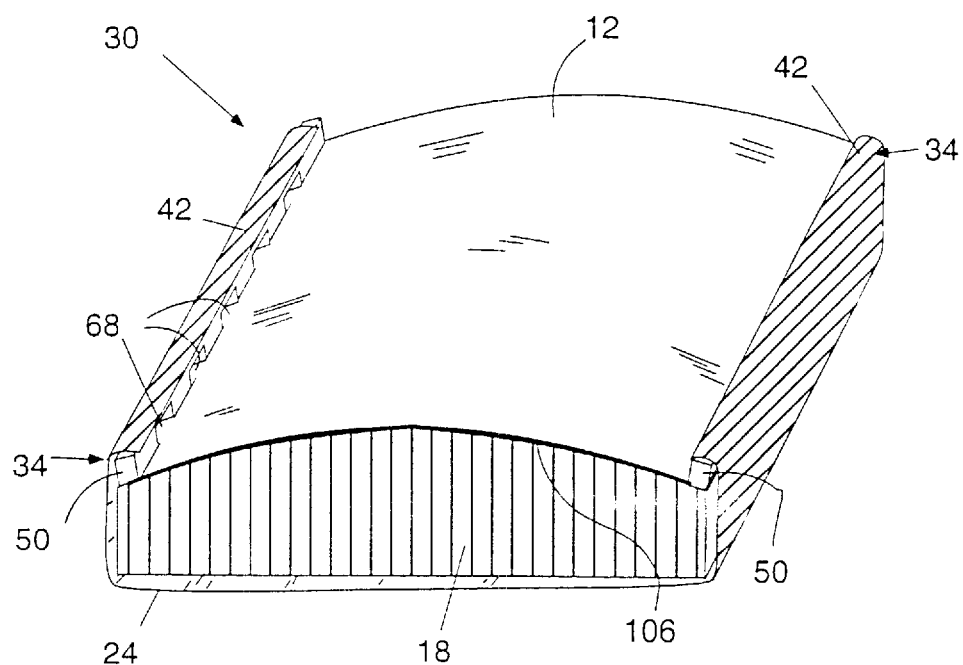
FIG. 5 is a perspective view of a portion of a portion of an absorbent core with a wicking barrier and wicking barrier cuffs on the body-side surface thereof further comprising spacer means to hold the wicking barrier cuff open.

FIG. 5 depicts a perspective view of a portion of an absorbent core 30 for use in articles such as a pantiliner. The central absorbent member 18 has a contoured shape to provide a central mound and is shown with a topsheet 12 (or other intake layer) attached to the upper surface of the central absorbent member 18. The wicking barrier 24 wraps the longitudinal sides of the central absorbent member 18 and thereafter extends laterally inward toward the longitudinal centerline on the body-side surface of the central absorbent member 18 to span a horizontal distance thereon. The portion of the wicking barrier 24 over the body-side surface of the central absorbent member 18 is the horizontal upper layer 42 of a wicking barrier cuff 34. The wicking barrier cuff 34 is provided with void spaces 68 for receiving fluid due to the presence of deformable spacer means 50 disposed between the body-side surface of the central absorbent member 18 and the horizontal upper layer 42 of the wicking barrier cuff 34. The deformable spacer means 50 is a longitudinal strip of a deformable, resilient material such as a polyurethane foam having spaced apart void spaces 68 forming channels therein to permit fluid to pass through the spacer means 50 and into the wicking barrier cuff 34 and from thence into the central absorbent member 18. Desirably, the void spaces 68 are at least 0.5 mm long in the longitudinal direction. As depicted, the void spaces 68 are not as tall as the spacer means 50 and do not completely separate the spacer means 50 into discrete segments due to a continuous section of the resilient material along the top of the spacer means. Alternatively, the spacer means 50 could comprise discrete segments of resilient material with open channels therebetween.

The body-side surface of the central absorbent member 18 as depicted is substantially covered by a topsheet 12, which need not extend completely to the longitudinal sides of the central absorbent member 18, but can leave a portion of the central absorbent member 18 under the spacer means 50 uncovered to improve uptake of fluid by the central absorbent member 18 from the wicking barrier cuff 34. In particular, it is desirable that the body-side surface of the central absorbent member 18 under the void spaces 68 in the spacer means 50 be substantially free of coverage from the topsheet 12 to permit rapid intake of fluid directly into the central absorbent member 18.

Alternatively, the topsheet 12 could be adhesively attached to the exposed surface of central absorbent member 18 and then rise to be disposed over the wicking barrier cuff 34 and be joined to the backsheet (not shown) or the wicking barrier 24 along the longitudinal sides of the absorbent article (not shown) or along any portion of the wicking barrier 24, in which case the topsheet 12 preferably should be provided with apertures in the vicinity of the spacer means 50 to permit easy entry of fluid into the void spaces 68. Apertures or other openings in the topsheet 12 desirably would be substantially the same size as the void spaces 68 in the spacer means 50 for reduced resistance to fluid entry into the wicking barrier cuff 34.

In production of an absorbent article from the absorbent core 30 of FIG. 5, the absorbent core 30 could further comprise an outer absorbent member (not shown) or additional absorbent material (not shown) at the longitudinal ends of the central absorbent member 18 or along the longitudinal sides thereof, and could further comprise a backsheet (not shown), though the wicking barrier 24 could function also as a portion of the backsheet in the region beneath the central absorbent member 18.

Figure 6:
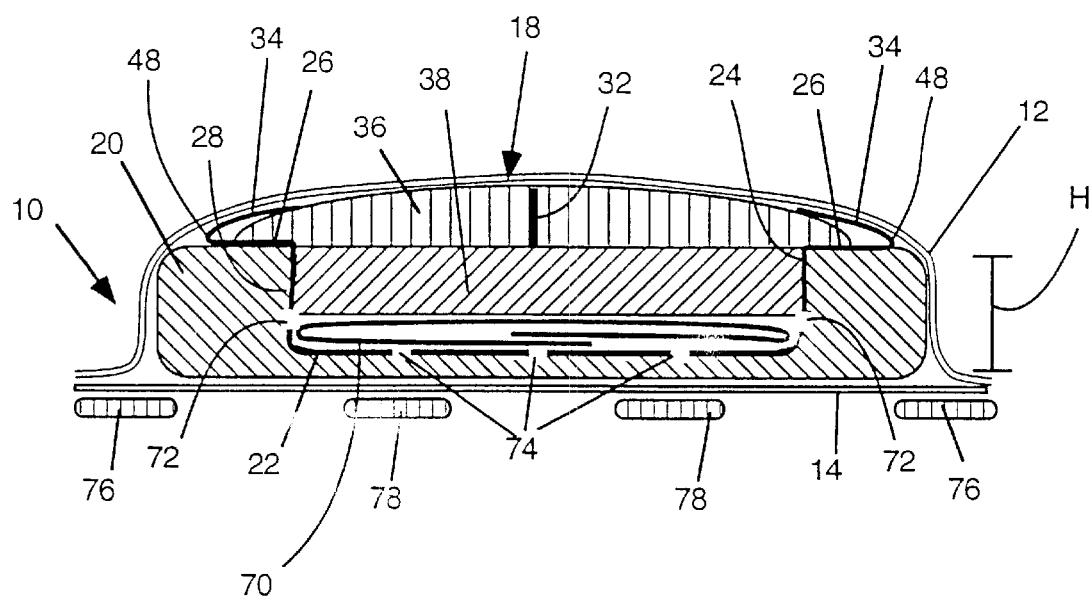
FIG. 6 is a transverse cross-section of an absorbent article according to the present invention comprising a wicking barrier cuff and a central rising member.

FIG. 6 depicts a transverse cross-section of another absorbent article 10 according to the present invention. The outer absorbent member 20 has a central region of reduced basis weight or thickness having a surface which defines the boundary of a central void 22 for receiving the central absorbent member 18, which comprises an upper absorbent layer 36 and a lower absorbent layer 38. A wicking barrier 24 separates the outer absorbent member 20 from the central absorbent member 18. A thin central rising member 70, depicted as an "e-folded" span of material, lies between the central absorbent member 18 and the wicking barrier 24. The central rising member 70 comprises a resilient web of material such as a layer of densified airlaid web or multiple layers of a stiff tissue web with sufficient resiliency that, when laterally compressed, the upward buckling or deformation of the folded web can deflect the central absorbent member 18 upward toward the body of the wearer.

The wicking barrier can be smooth and have relatively low friction, permitting sliding or motion of portions of the central rising member 70 relative to the wicking barrier 24 when the article 10 is laterally compressed. The relative motion of portions of the central rising member 70 relative to the wicking barrier 24 can be helpful in some embodiments, though the central rising member 70 can still drive upward deflection of the central absorbent member 18 during inwardly lateral compression if portions of the central rising member 70 in contact with the wicking barrier 24 are fixedly attached or unable to slide.

The wicking barrier 24 spans a vertical distance H between the elevation of the body-side surface of the outer absorbent member 20 and the elevation of the lowest portion of the surface of the central void 22 in the outer absorbent member 20. H can be from about 1 mm to about 10 mm, more specifically from about 1 mm to about 5 mm, and more specifically still from about 2 mm to about 4 mm. The wicking barrier 24 has a vertical component 28 (which need not be substantially vertical in orientation as shown but spans a vertical distance) and has a horizontal component 26 acting as a ledge and spanning a horizontal distance on the body-side surface of either the outer absorbent member 20 or the central absorbent member 18. The horizontal component 26 of the wicking barrier 24 may cover only a fraction of the exposed body-side surface of the outer absorbent member 20, as shown (e.g., less than 50% or less than 20% of the linear distance from a longitudinal edge of the central absorbent member 18 to the nearest outer longitudinal edge of the outer absorbent member 20), or it can cover substantially all of the body-side surface of the outer absorbent member 20 in any particular cross section, especially in the crotch region of the article, to prevent wicking contact of the central absorbent member 18 with the outer absorbent member 20 when the article is bunched up in use.

The horizontal component 26 of the wicking barrier 24 has been extended toward the longitudinal sides of the article 10 to a folding line 48 and thereafter folds back upon itself above the surface of the outer absorbent member 20 to create a wicking barrier cuff 34. The wicking barrier cuff 34 preferably is attached to the topsheet 12, which in turn is preferably lifted or pulled above the height of the outer absorbent member 20 by virtue of the body-side surface of the central absorbent member 18 being relatively more elevated. The wicking barrier cuff 34 desirably extends substantially in the longitudinal direction, and preferably extends longitudinally throughout all or a majority of the target zone or crotch region. The wicking barrier cuff 34 above the exposed portion of the outer absorbent member 20 can serve to capture fluid and prevent runoff, allowing fluid to be redirected toward the central absorbent member 18 or toward the longitudinal ends of the absorbent article 10, thus further serving to reduce leakage to the longitudinal sides. The wicking barrier cuff 34 can also serve in increasing the flexibility of the article by providing increased mobility between the wicking barrier 24 and the topsheet 12, with the wicking barrier cuff 34 acting as a slider or spring during deformation of the article 10.

The wicking barrier cuff 34 is partially held open by attachment to an elevated upper absorbent layer 36 of the central absorbent member 18 that extends on the surface of the absorbent core beyond the vertical component 28 of the wicking barrier 24 and rises substantially above the plane of the outer absorbent member 20. Thus, the wicking barrier 24, in folding back upon itself on the surface of the outer absorbent member 20, can receive absorbent material such as the upper absorbent layer 36 within the wicking barrier cuff 34. The upper absorbent layer 34 of the central absorbent member 18 desirably is a highly porous material and can be a surge layer, and desirably is provided with a shaping line 32 to promote or permit upper folding or flexing of the upper absorbent layer 36 during lateral compression. The upper absorbent layer 36 of the central absorbent member 18 need not fill the wicking barrier cuff 34 completely, but could be a thin tissue layer instead of the relatively thick, tapered upper absorbent layer 36 depicted and may comprise a corrugated material (i.e., a material with a scalloped edge to hold the wicking barrier cuff 34 open). Alternatively, the wicking barrier cuff 34 may have a scalloped edge (not shown) extending in the longitudinal direction to increase the open void volume for intercepting fluid flowing from the center of the article 10 toward the longitudinal sides thereof.

The upper absorbent layer 36 may extend longitudinally through the crotch region or past the crotch region toward the longitudinal ends of the article 10, if desired.

The lower absorbent layer 38 desirably has a smaller pore size than the upper absorbent layer 36 such that fluid tends to wick away from the upper absorbent layer 36 into the lower absorbent layer 38. The lower absorbent layer 38 may be a rectangular or other shaped insert comprising hydrophilic fibers such as airlaid or wet laid cellulose, including a pad of fluff pulp, crosslinked fibers, multiple layers of creped or uncreped tissue, peat moss, cotton, mixtures of absorbent fibers and superabsorbent particles or fibers, layers of fluff separated by tissue layers, or absorbent foams or foam-fiber composites. Desirably, the AUL value of the lower absorbent layer 38 is about 10 grams/gram or greater. In use, the central absorbent member 18 will tend to fill first with fluid, after which wicking or bulk flow of fluid to the surrounding or underlying regions of the outer absorbent member 20 can take place if sufficient fluid enters the absorbent article 10.

Flow of fluid from the central absorbent member 18 to the outer absorbent member 20 is made possible by the presence of optional apertures or openings 72, 74 in the wicking barrier 24 remote from the body-side surface of the article 10. It is intended that body fluid will primarily enter the absorbent article 10 in or immediately above the central absorbent member 18, first passing through topsheet 12. If fluid spreads radially from the central absorbent member 18 to the outer absorbent member 20, it is intended that such movement of fluid will occur by a tortuous pathway rather than by directly wicking from the body-side surface of the central absorbent member 18 to the body-side surface of the outer absorbent member 20. A tortuous path is established by the optional apertures or openings 72, 74 in the wicking barrier 24 such that fluid entering the central absorbent member 18 must first migrate downward to the openings 72, 74 in the wicking barrier 24 and from thence into the radially outward sections of the outer absorbent member 20, still submerged beneath the body-side surface of the outer absorbent member 20, thus keeping fluid away from exposed surfaces. The depth, size, and number of the openings 72, 74 can be adjusted to provide the proper balance between hindering laterally outward flow toward the edges of the article and preventing oversaturation and overflowing of fluid from the central absorbent member 18. The openings 72, 74 are not needed if the absorbent capacity of the central absorbent member 18 is adequate for the anticipated fluid loadings the absorbent article 10 will receive.

The outer surface of the backsheet 14 can be coated with adhesive such as the pressure-sensitive adhesive strips 76, 78. The adhesive, for example, can provide a means for securing the pad in the crotch portion of a panty. Any adhesive or glue used in the art for such purposes can be used herein, with pressure sensitive adhesives being preferred. Also, before sanitary napkin 10 is placed in use, the pressure sensitive adhesive should be covered with one or more removable release liners (not shown). Any commercially available release liners commonly used for such purposes can be utilized. In several embodiments, it is desirable that outer adhesive strips 76 be disposed as close as possible to the longitudinal sides of the article 10 to provide better attachment to the user's undergarments, thus reducing the tendency of side portions of the article 10 to bunch and come into liquid communication with the surface of the central absorbent member 18. One or more additional inner adhesive strips 78 can also be used for improved security. The outer adhesive strips 76 can be any useful width, such as from about 1 mm to about 15 mm, and more specifically from about 3 mm to about 10 mm.

The adhesive strips may further comprise microcapsules containing agents that are not released until the release liner is removed, which breaks some of the microcapsules, as taught in U.S. Pat. No. 5,591,146, issued Jan. 7, 1997 to Hasse, herein incorporated by reference. The microcapsules can contain odor control agents, perfumes, skin wellness agents, and the like.

It is desirable that the width of the central absorbent member 18 be from about 1 to about 12 centimeters, more specifically from about 2 to about 7 centimeters, and most specifically from about 2 to about 5 centimeters.

Figure 7A:
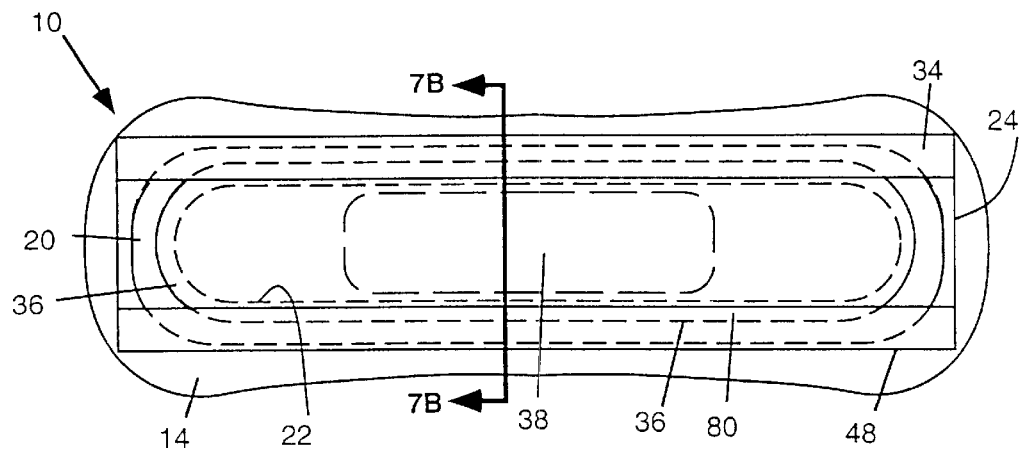
FIGS. 7A and 7B provide a top view and a transverse cross-sectional view, respectively, of an article with a wicking barrier cuff and a central absorbent member having a central pledget (lower absorbent layer in the central absorbent member) and a convex upward upper absorbent layer.
Figure 7B:
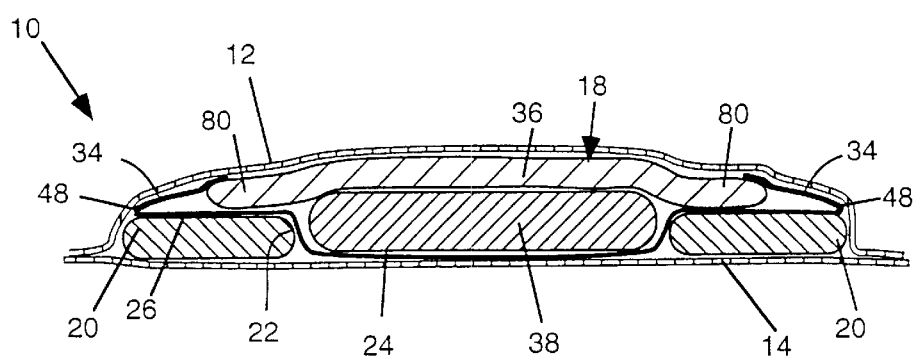

FIGS. 7A and 7B depict views of another absorbent article 10 according to the present invention. The topsheet 12 is not shown in the top view of FIG. 7A for clarity. FIG. 7B provides a transverse cross-section along the line depicted in FIG. 7A.

Superposed over the backsheet 14 is an annular ring of absorbent material serving as an outer absorbent member 20 having a central void 22. Within the central void 22 and directly over the backsheet 14 is a lower absorbent layer 38 which is a pledget of absorbent material such as fluff pulp having a thickness desirably greater than the thickness of the outer absorbent member 20. Disposed over the lower absorbent layer 38 and covering the central void 22 is an upper absorbent layer 36 which overlaps with a portion of the outer absorbent member 20 to define an overlap region 80. The lower absorbent layer 38 holds the upper absorbent layer 36 in a convex upward shape predisposed to flex vertically upward during laterally inward compression from the longitudinal sides of the article 10. The upper absorbent layer 36 is wider than the lower absorbent layer 38, and the latter is thicker than the outer absorbent member 20.

Lining the central void 20 and covering a portion of the outer absorbent member 20 is a wicking barrier 24 (a thin thermoplastic film) which is disposed beneath the lower absorbent layer 38. The polymeric wicking barrier 24 lines the central void 22 such that it lies beneath the lower absorbent layer 38 and separates the longitudinal sides of the lower absorbent layer 38 from the internal sides of the outer absorbent member 20. The wicking barrier reverses direction and folds back upon itself at a folding line 48, thereafter extending a distance back toward the longitudinal centerline of the article 10 to contact the body-side surface of the upper absorbent layer 36 of the central absorbent member 18 near the longitudinal sides thereof, thereby defining the wicking barrier cuff 34.

The wicking barrier cuff 34 can flex vertically upward during lateral compression to create an elevated loop of topsheet material 12 to create a dynamic bubble cuff (not shown), similar to that shown in FIG. 2B (labeled as 54).

Without limitation, further principles for construction of absorbent articles according to the present invention are given below in terms of the specific components.

The Absorbent Core

The absorbent materials of the absorbent core, including either the central absorbent member or the outer absorbent member or both, can comprise one or more plies of wetlaid or airlaid tissue; cellulosic airlaid webs of comminuted fibers (commonly termed "airfelt"); other dry laid webs; cellulose-superabsorbent mixtures or composites; hydroentangled webs comprising cellulosic fibers; composites of synthetic fibers and papermaking fibers; rayon; lyocell or other solvent-spun hydrophilic fibers, such as those disclosed in U.S. Pat. No. 5,725,821, issued Mar. 10, 1998 to Gannon et al.; cellulosic foams including regenerated cellulose foams; hydrophilic, flexible foams; fiber-foam composites; absorbent nonwoven webs; cotton; wool; keratin fibers; peat moss and other absorbent vegetable matter; the foam-structured fibrous absorbent materials of F.-J. Chen et al. disclosed in the commonly owned, copending U.S. patent application "Fibrous Absorbent Material and Methods of Making the Same," Ser. No. 09/083,873, filed May 22, 1998; or absorbent foams produced from high internal phase emulsions (HIPE) or other means, such as the foams disclosed in U.S. Pat. No. 5,692,939, issued Dec. 2, 1997 to DesMarais, U.S. Pat. No. 5,851,648, issued to K. J. Stone et al., Dec. 22, 1998, or in U.S. Pat. No. 5,795,921, issued Aug. 18, 1998 to Dyer et al. The absorbent materials of the absorbent core can also comprise corrugated absorbent materials for enhanced longitudinal transport of fluid, such as the materials disclosed in U.S. Pat. No. 4,578,070, issued Mar. 25, 1986 to Holtman. In a preferred embodiment, at least one layer of the absorbent core comprises cellulosic fibers and PET (polyethylene terephthalate) staple fibers, such as from about 5% to about 20% staple fibers by weight, to provide increased wet resiliency and integrity of the absorbent core.

A particularly useful cellulose-polymer composite material is coform, a hydraulically entangled mixture of pulp fibers and polymer, such as the materials disclosed in U.S. Pat. No. 4,879,170, issued Nov. 7, 1989 to Radwanski et al.; U.S. Pat. No. 4,100,324 to Anderson et al. issued Jul. 11, 1978, and U.S. Pat. No. 5,350,624 to Georger et al. issued Sep. 27, 1994, or the materials made by the methods of Lau et al. in U.S. Pat. No. 5,711,970 issued Jan. 27, 1998.

Any suitable form of cellulosic material can be incorporated in the absorbent materials of the absorbent core, including wood fibers, such as bleached kraft softwood or hardwood, high-yield wood fibers, and chemithermomechanical pulp fibers; bagasse; milkweed; wheat straw; kenaf; hemp; or peat moss. High-yield fibers can be used to make absorbent members, exemplified by the high-yield airfelt disclosed in U.S. Pat. No. 4,247,362, issued to J. C. Williams, Jan. 27, 1981. The fibers can also be crosslinked, sulfonated, mercerized, heat treated, mixed with thermoplastic stabilizer fibers, or treated with wet strength agents. Caustic-treated fibers, such as those made according to U.S. Pat. No. 5,858,021, "Treatment Process for Cellulosic Fibers," issued to Tong Sun and Sheng Hu, Jan. 12, 1999, can be especially beneficial in providing good absorbency and bulk properties. Mixtures of various fibers can be used, including coform, which comprises thermoplastic fibers and wood fibers deposited together in an airlaying process.

The article may also comprise hydrophobic material around the sides of the absorbent core to further reduce edge leakage. For example, hydrophobic fibers may be placed in discrete areas, such as around the periphery of the hydrophilic absorbent core, to provide barriers against leakage, as exemplified in U.S. Pat. No. 5,817,079, "Selective Placement of Absorbent Product Materials in Sanitary Napkins and the Like," issued to R. Bergquist et al., Oct. 6, 1998. A related approach which can be applied to the present invention is given by Csillag in U.S. Pat. No. 4,015,604, issued Apr. 5, 1977. An absorbent product is disclosed with side leakage control means comprising a narrow longitudinally extending zone along each side edge of the product but spaced away from each of the side edges. This zone is impregnated with a liquid hydrophobic material from the garment facing surface to the body facing surface of the product. The hydrophobic impregnate is applied to a hydrophilic pad as the pad passes through the manufacturing equipment. Likewise, Canadian Patent No. 884,608 issued to Levesque, Nov. 2, 1971, relates to treating the edges of a sanitary napkin product with hydrophobic material in order to prevent side leakage. In accordance with Levesque, the absorbent layer in the zone of the edges of the absorbent material is rendered hydrophobic while being maintained in a gas and moisture vapor permeable condition. The hydrophobic zone may be coated with a liquid repellent composition or chemically modified to render the fibers hydrophobic. In these embodiments with added hydrophobic fibers or hydrophobic matter toward the longitudinal sides of the absorbent core, it is nevertheless desirable that a wicking barrier such as a polymeric film passes over at least a portion of the surface of the hydrophobic areas in the crotch region of the absorbent core.

The absorbent core may also comprise a percentage of water-swellable minerals such as bentonite particles, vermiculite, and the like, preferably in the range of about 2% to about 40% by weight.

The Central Absorbent Member

The central absorbent member can comprise the same material as the surrounding outer absorbent member or can be a multi-ply assembly of wet laid tissue or a mixture of wet laid and air laid components, desirably also comprising superabsorbent material which may be laminated in pockets, adhesively attached to the plies, embedded in an airlaid layer, or present as fibers or films.

Dimensions of the components of the absorbent article can be suited and optimized for particular functions. For feminine care pads, for example, the outer absorbent member can have a transverse width (distance from one outer longitudinal side to the other across the transverse centerline, not the smaller edge width defined previously) of from about 4 cm to about 8 cm and a length of from about 15 cm to about 30 cm. The central void in the outer absorbent member may have a transverse width of from about 2 cm to about 6 cm, more specifically from about 3 cm to about 5 cm, and can have a length of from about 4 cm to about 30 cm, more specifically from about 6 cm to about 20 cm, resulting in a desirable distance from the longitudinal edge of the central absorbent member to the nearest outer longitudinal edge of the outer absorbent member (which can also be the edge width of the outer absorbent member, assuming no significant gap between the outer absorbent member and the central absorbent member) of from about 0.3 cm to about 2.5 cm, and more specifically from about 0.5 cm to about 2 cm, and more specifically still from about 0.7 cm to about 1.5 cm. Appropriately larger dimensions would be desirable for diapers and many other absorbent articles. For example, the central absorbent member may be from about 4 cm to about 10 cm in width in a diaper.

Basis weights of the components of the absorbent core can be adjusted and optimized for particular purposes over a wide range. Generally, it is desirable that the basis weight of the central absorbent member be greater than the outer absorbent member because the central absorbent member is intended to contain the primary source of absorbent material for the article, and the outer absorbent member can desirably function as a secondary source of absorbent material when the absorbent capacity of the central absorbent member is exceeded. Thus, the basis weight of the central absorbent member can range, for example, from about 100 grams per square meter (gsm) to about 2500 gsm, more specifically from about 200 gsm to about 1200 gsm, and more specifically still from about 300 gsm to about 800 gsm. The basis weight of the outer absorbent member (or, in some embodiments, of the outer shaping member) can range from about 100 gsm to about 2000 gsm, more specifically from about 200 gsm to about 1000 gsm, and most specifically from about 200 gsm to about 600 gsm.

The absorbent capacity of either the central absorbent member or the outer absorbent member can be optimized for the intended use of the article. In diapers, the absorbent capacity of the central absorbent member generally should be greater than 60 ml and can be about 300 ml or less of fluid, more specifically about 200 ml or less, more specifically still about 150 ml or less, with exemplary ranges of from about 80 ml to about 250 ml or from about 100 ml to about 300 ml. For some uses, such as in sanitary napkins, it is desirable that the absorbent capacity of the central absorbent member be at least 7 ml of fluid, specifically at least 10 ml, more specifically at least 16 ml, more specifically still at least 20 ml, and most specifically from about 15 ml to about 35 ml. In one embodiment, the absorbent capacity of the outer absorbent member is less than the absorbent capacity of the central absorbent member. For example, the outer absorbent member can have an absorbent capacity of about 5 to about 100% of the absorbent capacity of the central absorbent member, or the ratio can be about 90% or less, more specifically about 70% or less, and more specifically still about 30% or less. If desired, however, the outer absorbent member can have a higher absorbent capacity than the central absorbent member. In a less preferred embodiment, the outer absorbent member can have relatively little absorbent capacity, such as between about 1 ml to about 5 ml, but can primarily serve to provide a body-fitting shape to the article and to retain the central absorbent member and the wicking barrier. A ring of a flexible polyurethane foam would be an example of a less absorbent outer member that could serve such a purpose, even if it were a closed-cell foam, but it is preferred that the outer member be relatively absorbent to provide additional protection and absorbency to the article, in addition to optionally serving other functions such as body fit, comfort, integrity of the article, and wetness indication.

For ultrathin pads and other absorbent articles, it is desirable that the dry components of the absorbent core have a total thickness between about 2 mm and about 15 mm, and more specifically from about 3 mm to about 8 mm. When wetted, the central absorbent member and/or the outer absorbent member can increase substantially in thickness and void volume, such as a thickness increase of about 100% or greater, more specifically about 200% or greater, and more specifically still about 300% or greater. Means for causing volume increase in the article include the use of densified flash-dried high-yield fibers, creped tissue restrained against a stability layer at spaced apart points or lines, calendered three-dimensional tissue webs comprising high-yield fibers, regenerated cellulose materials or other densified foam or sponge materials, compressed chemically stiffened fibers such as crosslinked fibers, and the like. Further details on volume increasing means are discussed below in connection with spacer means for the wicking barrier.

Either the central absorbent member or the outer absorbent member or both, or individual plies thereof, may be embossed for improved control over fluid wicking, if desired. The absorbent members likewise may be apertured, slitted for improved flexibility and body conformability, perf-embossed, calendered, or pleated. A central slit in the central absorbent member can be especially useful in products for feminine care, for the slit can result in deformation of the article in use that enhances contact with the body for better absorption of menses.

The central absorbent member generally can be of any shape such as circular, elliptical, rectangular, triangular, polygonal, dog-bone shaped, hourglass shaped, or diamond shaped, and is inset or inserted into a depression or void in an outer absorbent member having either a width or length, or both, greater than the respective width or length of the central absorbent member. The central absorbent member desirably has a longitudinal length greater than the width, with the length extending desirably across 30% or more of the length of the article, more specifically 50% or more, more specifically still 75% or more, and most specifically 90% or more of the length of the absorbent article, including 100% of the length of said article. The central absorbent member can be substantially as long as the absorbent core, or can have a length ranging from about 10 mm to about 170 mm. Especially in embodiments where the longitudinal ends of the central absorbent member are contained within a longer outer absorbent member, the length of the central absorbent member can be from about 20 mm to about 140 mm, more specifically from about 40 mm to about 100 mm, and most specifically from about 60 mm to about 85 mm. The maximum width of the central absorbent member can be 100% of the width of the absorbent article but desirably is no more than about 90%, more specifically no more than about 75%, and more specifically still no more than about 60% of the width of the absorbent article. The absorbent article in the crotch region generally can have a width of about 20 mm or greater, more specifically about 40 mm or greater, and more specifically still about 60 mm or greater. For absorbent articles without a crotch region, the width can be any of the following exemplary ranges: from about 20 mm to about 500 mm; from about 40 mm to about 100 mm; about 150 mm or greater; from 7 mm to about 35 mm; or from about 10 mm to about 100 mm.

The central depression or void of the outer absorbent member is desirably a region of reduced basis weight relative to the other regions of the outer absorbent member, but can also be a region which has been compressed in thickness substantially such that a depression is defined which can receive an absorbent insert to serve as a central absorbent member.

The central absorbent material may be two or more strips of cellulosic material, such as an upper strip of an airlaid or wetlaid material having a first density or mean pore size and a second lower strip of an airlaid or wetlaid material having a second density or mean pore size. Desirably, the mean pore size of the lower strip is smaller than that of the upper strip such that capillary forces will preferentially remove fluid from the upper strip into the lower strip for an improved dry feel. In one embodiment, the lower strip is a wet laid material such as a through-dried tissue having a density greater than 0.1 grams per cubic centimeter (g/cc) and suitably greater than about 0.15 g/cc, while the upper strip is an air laid material having a density less than about 0.15 g/cc and specifically less than about 0.1 g/cc. The combined basis weight of the central absorbent strip or strips can be greater than, less than, or about the same as that of the surrounding outer absorbent member, with characteristic values between about 50 and 500 gsm, specifically between about 100 and 400 gsm, and more specifically between about 150 and 300 gsm. Desirably, though, the central absorbent member has a substantially higher basis weight than the outer absorbent member for better efficiency in material usage.

The central absorbent member can also comprise a central opening or aperture (known as a "port hole," especially in European markets), exemplified by the teachings of German patent application No. 19640451. The port hole may be filled with a pouch of free-flowing particles or may remain open for intake of viscous fluid. The port hole structure, such as an absorbent ring of material encompassing a central opening, can then be isolated from the outer absorbent member by a wicking barrier. A central rising member can be disposed in or beneath the opening in the central absorbent member such that absorbent material can rise above or through the opening in the central absorbent member during lateral compression to provide better contact with the body and to improve the intake function of the central absorbent member and the port hole structure.

The central absorbent member may be tapered with sides that overlap a portion of the outer absorbent member, with the tapered sides being above or below the outer absorbent member. For example, a central absorbent member comprising a central rising member, such as a pre-shaped pledget of fluff pulp predisposed to flex upward when laterally compressed, may have thin side portions that extend beneath the outer absorbent member (i.e., the transverse width of the central absorbent member can be greater than the transverse width of the central void or depression in the outer absorbent member). In such an embodiment, the wicking barrier can wrap the longitudinal sides of the central absorbent member beneath at least a portion of the outer absorbent member and then rise along the inner walls of the central void or depression in the outer absorbent member to isolate the central absorbent member from the outer absorbent member.

The central absorbent member can comprise multiple layers. In one preferred embodiment, the central absorbent member comprises a top intake layer, which may be a tissue layer or other absorbent material adapted for rapid intake of fluid, a longitudinal wicking layer for effective transfer of liquid in the longitudinal direction, and a lower fluid retention layer, which may comprise superabsorbent material, densified pulp fibers, microstrained pulp sheets, tissue, coform, or peat moss. The longitudinal wicking layer can comprise densified airlaid strips having a longitudinal length greater than their transverse width; wet laid tissue with a mean fiber orientation predominately in the longitudinal direction; a plurality of other absorbent strips or filaments.

The central absorbent member can comprise between about 10% and 90% of the mass of the absorbent core on a dry basis, more specifically between about 20% and 70%, more specifically still between about 20% and 60%, and most specifically from about 25% to less than 50%.

The Outer Absorbent Member

The outer absorbent member can comprise the same absorbent materials as the central absorbent member or other absorbent materials known in the art, with cellulosic fibers being desirable for their low cost, good visual and tactile properties, good absorbent capacity, and biodegradability. Desirably, the outer absorbent member is fibrous with fibers that are essentially discontiguous with the central absorbent member (i.e., the central absorbent member and the outer absorbent member do not share fibers that join the two members). The outer absorbent member desirably has a lower basis weight than the central absorbent member but still provides several important functions. Generally, it is intended that the outer absorbent member remain unwetted except in cases of heavy flow. The unwetted structure of the outer absorbent member does not collapse but maintains high integrity in the dry state, which helps maintain the shape and fit of the article. When it does become wetted, the outer absorbent member can serve as an indicator that the absorbent article needs to be replaced.

For both the outer absorbent member and the central absorbent member, if the absorbent member is comprised of more than one constituent part or material, one part or material of the absorbent member may not be absorbent or liquid permeable, so long as the combination of parts or materials has some degree of absorbency and some degree of the properties set forth above. Desirably, however, the majority of the material by mass is absorbent and more desirably at least about 90% of the material of the absorbent member is inherently absorbent. In one embodiment, substantially all of the absorbent member is composed of absorbent material.

The Wicking Barrier

The wicking barrier can comprise any barrier material that substantially reduces lateral wicking of fluid from the central absorbent member to the surrounding outer absorbent member. The barrier spans a finite vertical distance in the absorbent article, such as about 2 mm or greater, specifically about 3 mm or greater, more specifically about 5 mm or greater, and most specifically from about 4 mm to about 15 mm. The barrier material can be a polymeric film or plastic film; a nonwoven web; a layer of rubber, silicone, or other non-absorbent materials; or a less pervious paper sheet including, for example, glassine, wax paper, impregnated papers, paper-polymer composites, paper or tissue containing internal sizing to render it substantially hydrophobic, paper or tissue treated with (e.g., coated with) hydrophobic matter such as wax, silicone, thermoplastic material, or polyolefins. Flexible hydrophobic foams may also be used, such as a closed-cell polyurethane foam or a silicone foam.

Desirably, the barrier material will have a porosity less than 90%, specifically less than 50%, more specifically less than 30%, and more specifically the barrier material will be substantially nonporous or substantially impermeable, though a small number of apertures or small openings can be provided in selected portions of the barrier material to prevent oversaturation of the central absorbent member. Suitably, the thickness of the wicking barrier can be about 2 mm or less, more specifically about 1 mm or less, and most specifically about 0.5 mm or less. In some cases, such as when a barrier material in the form of a flexible polymer sheet is used, including a polypropylene or polyethylene web, the barrier material can have a thickness of about 0.2 mm or less, more specifically about 0.1 mm or less, and most specifically about 0.08 mm or less, with an exemplary range of from about 0.02 mm to about 0.3 mm.

Desirably, the Intrinsic Absorbent Capacity of the barrier material is about 1 or less, more specifically less than about 0.5, more specifically still less than about 0.3, and most specifically less than about 0.1. The barrier material desirably is substantially non-absorbent.

In one embodiment, the wicking barrier is integral or unitary with the backsheet, and comprises an extended portion of the backsheet which wraps a portion of the outer absorbent member and desirably is away from the body-side surface of the absorbent core by virtue of spacer means.

In some embodiments, the wicking barrier need not be hydrophobic and can even be absorbent as long as wicking is substantially hindered by a barrier function provided by the wicking barrier. For example, a liquid impervious film of superabsorbent material such as a polyacrylate film can be used. The film may swell and absorb water without permitting wicking flow to extend beyond the film.

The wicking barrier cuff or other portions of the wicking barrier can be provided with attached hydrogel or superabsorbent material on the side toward the longitudinal centerline at the body-side surface in order to take up fluid in addition to impeding the wicking and flow of fluid past the wicking barrier.

Spacer means for the wicking barrier cuff are desirable in many embodiments to help keep the wicking barrier cuff open, even under compressive forces, in order to permit the wicking barrier cuff to receive fluid. A variety of spacer means are discussed above, including attachment of an upper portion of the folded wicking barrier to a structure at a substantially higher elevation than the lower portion of the folded wicking barrier; spacers of absorbent material or non-absorbent material to keep the two layers of barrier material apart; and corrugations, wrinkles, embossments, apertured cones, ribs, or other three-dimensional elements in or on the wicking barrier.

Absorbent materials inserted into the wicking barrier cuff, either throughout the longitudinal length of the cuff or at spaced apart intervals, can be especially useful for achieving good performance, particularly when the absorbent material further can expand in the z-direction when wetted to provide increased fluid management performance and body fit. Thus, a volume increase in absorbent material upon wetting can not only be used to improve retention and body fit in the absorbent materials of absorbent articles such as ultrathin pads, but can also be used to add void volume to wicking barrier cuffs. Thus, a volume increase upon wetting can be used to increase the space between an upper and lower layer of a wicking barrier cuff or increase the contact between the body and the wicking barrier cuff or dynamic bubble cuff.

An example of a low-cost cellulosic component capable of increasing in thickness when wet is the absorbent material of Chen and Lindsay disclosed in U.S. Pat. No. 5,865,824, "Self-texturing Absorbent Structure and Absorbent Articles Made Therefrom," issued Feb. 2, 1999. In the articles disclosed therein, creped tissue layers or other materials that tend to expand in the plane of the article when wetted are heterogeneously attached to a stability layer such as a polymeric film which does not expand significantly upon wetting. The in-plane expansion of the tissue when wetted coupled with the restraint offered by spaced apart attachments to the stability layer results in puckering or pocket formation between the attachment regions, leading to increased void volume and the possible formation of flow channels between the tissue or "expansion layer" and the stability layer. The stability layer disclosed therein can also serve as a wicking barrier or as a portion of the wicking barrier in the present invention. Thus, in one embodiment, spacer means in the wicking barrier cuff could include one or more plies of a creped tissue, preferably creped and embossed to provide more initial void volume in the wicking barrier cuff, which has been heterogeneously attached to one layer of the wicking barrier cuff, preferably the lower layer, such that upon wetting, the tendency of the creped tissue to expand in the machine direction of the web coupled with the spaced apart restraint offered by heterogeneous attachment to the wicking barrier material translates into puckering in the wicking barrier cuff to life it and provide more void volume. Desirably, the machine direction of the creped web is substantially aligned with the longitudinal direction of the absorbent article to give a corrugated effect in the wicking barrier cuff that provides opening toward the longitudinal centerline for receiving fluid.

Another absorbent material which expands significantly in the z-direction upon wetting is densified through-dried webs comprising high-yield fibers or calendered uncreped through-air dried webs having highly textured structures prior to calendering, such as the structures of Hollenberg et al. in U.S. Pat. No. 5,779,860, "High-density Absorbent Structure," issued Jul. 14, 1998. Regenerated cellulose sponge materials (including compressed cellulose sponges and HIPE foams) are also capable of expanding significantly when wet. Densified cross-linked cellulosic mats can also be used for the spacer means and for any absorbent member, as can crosslinked cellulosic fibers in general, and can include the webs and structures disclosed in any of the following patents: U.S. Pat. No. 5,360,420, issued Nov. 1, 1994 to Cook et al.; U.S. Pat. No. 5,324,575, issued Jun. 28, 1994 to Sultze et al.; and U.S. Pat. No. 5,217,445, issued Jun. 8, 1993 to Young et al. Compressed or densified flash-dried fibers in mat form or as chips or chunks, particularly high-yield fibers such as BCTMP, can increase substantially in volume when wetted and thus increase the void volume of the article and the void volume in the wicking barrier cuffs. Hydrogel or superabsorbent particles can also be used in the wicking barrier cuff to absorb fluid and cause expansion of the cuff, particularly if heterogeneously distributed to prevent gel block throughout the cuff.

Desirably, the spacer means separate the upper layer of the wicking barrier from the lower layer of the wicking barrier by at least 0.2 mm, specifically about 0.5 mm or greater, more specifically about 1 mm or greater, and most specifically about 2 mm or greater. Likewise, the spacer means desirably separate the upper layer of the wicking barrier cuff from the surface of the outer absorbent member (or the surface of another absorbent member that is directly underneath the upper layer of the wicking barrier cuff) by about 0.5 mm or greater, specifically by about 1 mm or greater, and more specifically by about 3 mm or greater. In one embodiment, spacer means other than a central absorbent member or other than an absorbent layer of the absorbent core are present which provide openings for receiving fluid flow in the wicking barrier cuff having a height in the open space of about 0.2 mm or greater, specifically about 0.5 mm or greater, more specifically about 1 mm or greater, and most specifically about 1.5 mm or greater. Thus, in one embodiment, the spacer means separate the upper layer of the wicking barrier from body-side surface of the absorbent member to provide a plurality of openings for receiving fluid in the wicking barrier cuff with any of the aforementioned heights.

Superabsorbent Material

The absorbent cores of the present invention can comprise superabsorbent particles, such as from 5% to 90% by mass superabsorbent particles on a dry mass basis, or from about 30 to about 70% superabsorbent particles, alternatively from about 10% to about 50% superabsorbent particles and more specifically from about 10% to about 40% superabsorbent particles. Superabsorbent material can be incorporated as loose particulates, particles bound to the hydrophilic fibers, superabsorbent fibers, or as a component of the binder material or structuring composition. Superabsorbent material can also be provided in the form of a foam, as disclosed in U.S. Pat. No. 5,506,035, "Superabsorbent Polymer Foam," issued to Van Phan et al., Apr. 9, 1996, or incorporated into the void spaces of an absorbent foam.

Superabsorbent particles are typically provided in a matrix of fluff fibers, and can be designed to absorb liquid rapidly or slowly, permitting a balance between the competing needs of rapid uptake of fluid and time required for effective distribution of the fluid by wicking. Exemplary uses of superabsorbent particles in absorbent articles are disclosed in U.S. Pat. No. 5,147,343, "Absorbent Products Containing Hydrogels with Ability to Swell Against Pressure," issued to Kellenberger, Sep. 15, 1992. All superabsorbent materials and hydrocolloids known in the art can be used.

Central Rising Member

The central rising member is a structure beneath or within the central absorbent member and above the backsheet which causes the central absorbent member (or at least a portion thereof) in the crotch region of an absorbent article to deflect upward when the absorbent article is laterally compressed in the crotch region from the longitudinal sides of the article. Desirably, the central rising member can be a flexible absorbent material such as densified airlaid pulp fibers, coform, or one or more layers of creped or uncreped tissue, adapted with bending lines, scoremarks, flexure points, and/or folded sections such as an "e"-folded web such that lateral compression from the longitudinal sides of the central rising member causes at least a portion of the central rising member to deflect upwards with sufficient force or resiliency that the overlying central absorbent member can be deflected or urged toward the body. An absorbent central rising member can also be configured as a flattened tube or an equivalent.

Many other materials can be used to construct a suitable central rising member. Moldable foams can be used, such as a polyethylene foam sheet which is subjected to thermomolding at a temperature of from about 110° C. to about 205° C. to form the central rising member, and desirably subsequently creased or scored to provide bending lines therein. Other suitable foams are made from such substances as polyethylene, polypropylene, polyester, polybutylene, ethylene vinyl acetate, polyurethane, thermobondable cellulose, latex, silicone elastomerics and others. The central rising member can also be made of various fibers, films or sheets of cellulose, rayon, nylon, polyester, stiffened cotton, polyethylene, vinyl acetate, latex, rubber, crosslinked natural rubber foams, plastic, heavy-weight paper such as cardboard, coated paper, or a combination or laminate of these or other materials. However, in many embodiments it is preferred that the central rising member be substantially absorbent and more specifically comprise at least 50% by weight of cellulosic fibers.

For best results, the central absorbent member should be able to buckle upward or deflect upward without being substantially restrained by the outer absorbent member. Desirably, the central absorbent member can deflect, buckle, or translate upwards in use somewhat independently of the outer absorbent member and desirably substantially independently, as can be achieved by completely separating the absorbent material of the central absorbent member from that of the outer absorbent member in the crotch region, at least along the longitudinal sides of the central absorbent member in the crotch region. Thus, in one preferred embodiment, the central absorbent member is substantially unattached to the central absorbent member apart from the common restraint offered by the backsheet, topsheet, or other components. When the absorbent material of the central absorbent member in the crotch region of the absorbent article is separated from the absorbent material of the outer absorbent member by a wicking barrier in particular, excellent benefits can be obtained from a central rising member beneath the absorbent core and specifically beneath the central absorbent member. Thus, the wicking barrier can physically separate the absorbent material of the central absorbent member from the outer absorbent member, allowing the absorbent materials thereof to be substantially unattached, regardless of the possible indirect attachment that can occur if both sides of the wicking barrier are provided with adhesive. With a suitable wicking barrier present, the central absorbent member can deflect and conform to the body without being significantly restrained by the outer absorbent member. Further, the wicking barrier helps prevent lateral liquid flow for combined good fluid handling and good body fit. Improved comfort and reduced product stiffness is also provided by the separation of the central absorbent member and the outer absorbent member, and further by the presence of a flexible wicking barrier, particularly one which reduces friction between the central absorbent member and outer absorbent member, such as a polymeric film or specifically a substantial smooth polymeric film with a thickness less than about 50 microns.

When the central rising member is absorbent and has adequate absorbent capacity, the absorbent central rising member itself can serve as the central absorbent member, in which case the central rising member and the central absorbent member are identical and generally only a portion of the central rising member would be deflected toward the body of the user during inwardly lateral compression in use. As used herein, a central rising member can be said to be "within" the central absorbent member when the two members are identical (at least in the mathematical sense that the entirety of a set is contained within a set) as well as when the central rising member is one of several components contained within the periphery of (or encased by) the absorbent material of the central absorbent member. In a preferred embodiment, however, an absorbent central rising member is beneath a separate layer of absorbent material that serves as the central absorbent member. In another embodiment, the central absorbent member is a web of absorbent material wrapped around a central rising member, such that inwardly lateral compression of the absorbent article causes the central rising member to buckle upwards and thus urge the portion of the central absorbent member lying above the central rising member toward the body of the wearer.

In a preferred embodiment, the density of the central rising member is substantially greater than the density of the outer absorbent member or of the central absorbent member. For example, the density of the central rising member may be about 0.1 g/cc or greater, more specifically about 0.3 g/cc or greater, and most specifically about 0.5 g/cc or greater, with an exemplary range of from about 0.35 g/cc to about 1.3 g/cc. It may be primarily cellulose such as tissue, paperboard, or an airlaid web; synthetic fibers, film, or sheets of polymers such as polyolefins, polyesters, nylon and other polyamides, and the like. In one embodiment, the density of the central rising member is about 30% greater than that of the outer absorbent member, and more specifically about 50% greater.

By way of example, the central rising member whether fibrous or not can have a basis weight of from about 30 grams per square meter (gsm) to about 800 gsm, more specifically from about 50 gsm to about 500 gsm, more specifically still from about 50 gsm to about 300 gsm, and most specifically from about 70 gsm to about 270 gsm.

Desirably, the central rising member comprises a at least one ply of a resilient material having a wall thickness, an internal void within the resilient material present due to folding or layering of the material, wherein the z-direction thickness of the internal void increases in size during lateral compression as the upper surface of the central rising member is displaced upward. Alternatively, the central rising member can lack an internal void, being a single layer of material that is folded or creased to form an inverted V-shape or U-shape when the longitudinal sides thereof are moved inward toward the initial longitudinal centerline of the central rising member.

In one embodiment, the central rising member can be a flattened, rolled tissue or paper structure including "e"- folded materials, with a centerline aligned with the longitudinal axis of the article (the flat cross-bar of the "e"-shape lying in the transverse direction, normal to the longitudinal axis of the article). Upon lateral compression from the longitudinal sides of the article, the flattened "e"-shape deflects upwardly, the upper loop of the "e"-shape springing back into the approximate shape of a semicircle to urge the upper surface of the central absorbent member toward the body of the wearer.

Desirably, the interaction of the central rising member with the central absorbent member and outer absorbent member results in an absorbent article well shaped for good fit against the body of the wearer. For sanitary napkins, the absorbent article when worn can assume any of the body-fitting shapes proposed by Lassen et al. in U.S. Pat. No. 4,804,380, "Anatomically Shaped, Self-Aligning, Sanitary Protection Device," issued Feb. 14, 1989, and in U.S. Pat. No. 4,846,824, "Labial Sanitary Pad," issued to Jul. 11, 1989.

The Topsheet

The topsheet has a body-facing side and a core-facing side. The body-facing side of the topsheet generally forms at least a portion of the body surface of the article. The topsheet should permit liquids to readily transfer through its thickness toward the absorbent core. The topsheet can comprise any fluid pervious cover material known in the art, such as nonwoven webs or apertured films, or other materials such as hydrophilic wet laid basesheets treated with portions of hydrophobic matter, including those of Chen et al. in commonly owned U.S. Pat. No. 5,990,377 issued Nov. 23, 1999 "Dual-zoned Absorbent Webs". Nonwoven webs used to produce a topsheet can include layers of spunbond material, meltblown material, and combinations thereof. The nonwoven webs may be apertured or slitted webs or provided with treatments for improved wettability, including corona discharge treatment, or treatments for improved flow permeability, such as hydroentangling or aperturing or microembossing. The topsheet can comprise a layer of a perf-embossed or apertured film on the body side bonded to a layer of a nonwoven web, preferably treated to be hydrophilic, on the core side. Similarly, the topsheet can comprise two or more nonwoven layers or film and nonwoven layers that have been co-apertured to provide apertures suitable for rapid intake of viscous or viscoelastic fluids and to improve wicking contact with underlying absorbent materials. Examples of suitable co-apertured materials are disclosed in U.S. Pat. No. 5,188,625, issued Feb. 23, 1993 to Van Iten et al. If apertured, the topsheet can have about 5 to about 60 percent open area and a thickness of about 0.01 to about 0.1 mm for a film or from about 0.03 to 0.5 mm for a fibrous nonwoven web.

The topsheet desirably is flexible and nonirritating to the wearer's skin. As used herein the term "flexible," in the context of films and hydrophobic webs, refers to materials which are compliant and readily conform to the shape of the body or respond by easily deforming in the presence of external forces. Preferably the topsheet is not noisy, to provide discretion for the wearer. The topsheet desirably can be somewhat opaque to hide the bodily discharges collected in and absorbed by the absorbent core. The topsheet can further exhibit good strikethrough and a reduced tendency to rewet, permitting bodily discharges to rapidly penetrate the topsheet to the core, but not allowing such discharges to flow back through the topsheet to the skin of the wearer.

Exemplary topsheets can be made in accordance with U.S. Pat. No. 5,533,991, issued Jul. 9, 1996 to Kirby et al.; U.S. Pat. No. 4,342,314 issued Aug. 3, 1982 to Radel et al. and U.S. Pat. No. 4,463,045 issued Jul. 31, 1984 to Ahr et al. The topsheet may comprise an additional transfer layer to help direct fluid into the absorbent core, as disclosed, for example, in U.S. Pat. No. 4,397,644, issued Aug. 9, 1983 to Matthews et al. The topsheet may comprise one or more layers of microdenier fibers, such as those disclosed in European Patent Application 893,517-A2, "Micro-Denier Nonwoven Materials Made Using Modular Die Units," A. Fabbricante, et al., published Jan. 27, 1999.

In one embodiment, the topsheet is a spunbond or other nonwoven web made from synthetic fibers, which has been spot bonded and apertured in the central portion. Desirably, the aperturing and spot bonding are done at the same time such that fibers are bonded together in the tapered sides of conical apertures.

In one embodiment, the topsheet comprises a soft nonwoven layer and an apertured film layer to provide a macroscopically heterogeneous cover, such as the cover constructions disclosed in European Patent Application 612,233-B1, "Absorbent Article with Comfortable and Rapid Acquisition Topsheet," K. Sugahara, Mar. 24, 1996 or other heterogeneous cover structures known in the art. For example, a nonwoven web with a central opening having a diameter of about 1 cm or greater can be disposed over an apertured film such that the soft nonwoven layer contacts the user's body away from the target area (e.g., the interlabial region), offering comfort and softness, while the apertured film contacts the body in the target area for controlled intake or cleanness. The apertured film need be only slightly larger than the opening in the topsheet to provide sufficient overlap for adhesive or thermal bonds to the nonwoven web to join the two layers.

The Backsheet

In the embodiments requiring a separate backsheet, the backsheet should strong enough for handling and flexible enough to fit body contours comfortably. The backsheet has a core-facing side and a garment side. At least a portion of the core-facing side of the backsheet will ordinarily face the core. Generally, the backsheet may be any flexible, liquid impervious material that prevents discharges collected by the absorbent article, such as a sanitary napkin, from escaping the absorbent article and soiling the undergarments and clothing of the wearer. Preferably, the backsheet is not noisy to provide discretion for the wearer. The backsheet can also be impervious to malodorous gases generated by bodily discharges, so that the malodors do not escape and become noticed by the wearer and others. The backsheet can comprise any material known in the art of absorbent articles, including polymeric films, low-permeability nonwoven webs, cloth layers desirably comprising an impervious layer or film, or polymer-tissue composites.

The backsheet and other components may be biodegradable and/or flushable.

Breathable films can be placed in a wide variety of regions in the article, including backsheets generally, as well as side, front or rear panels. Any breathable film material known in the art may be used. For example, U.S. Pat. No. 3,156,242 issued to Crowe, Jr. on Nov. 10, 1964 teaches the use era microporous film as a breathable backsheet. U.S. Pat. No. 3,881,489, issued to Hartwell on May 6, 1975, teaches a breathable backsheet comprising in combination two layers, the first of which is a low void volume perforated thermoplastic film and the second of which is a porous high void volume hydrophobic tissue. U.S. Pat. No. 3,989,867 issued to Sisson on Nov. 2, 1976 teaches a breathable backsheet provided with tapered hollowed bosses which prevent the passage of liquids while allowing vapors to pass through.

Breathable films can incorporate hydrophobic polymers which permit moisture transport through micropores. Micropores and other openings for vapor transmission can also be added when not inherently present by methods such as electric sparking or plasma etching; ultrasonic treatment; stretching of a film after inclusion of filler particles, bubbles, immiscible polymers, or other defects to create voids; laser drilling; fine embossing to create regions of high deformation in a web; and other techniques. Elastomeric films and webs can also be rendered breathable by inclusion of suitable hydrophilic polymers and/or addition of micropores by other means. The backsheet need not be breathable everywhere, but can be provided with a variety of zones having different degrees of breathability, including some regions that are not breathable.

The backsheet may also be extensible or elastically deformable for use in extensible absorbent articles. Any methods known in the art for production of elastic or stretchable films or cover sheets may be used, including those disclosed in U.S. Pat. No. 5,702,378, issued to Widlund et al., Dec. 30, 1997 and in U.S. Pat. No. 5,824,004, issued Oct. 20, 1998 to Osbom, III et al.

Other Configurations and Additional Components

The absorbent articles of the present invention can be combined with other functional materials internally (as by adding material into the absorbent material or on the barrier material) or externally (as by joining with additional layers), including but not limited to odor absorbents, activated carbon fibers and particles, baby powder, zeolites, perfumes, fire retardants, superabsorbent particles, nonwoven materials, plastic films or apertured films, extruded webs, closed cell foams, adhesive strips and tapes, tissue webs, electronic devices such as alarms indicating wetness or leakage and other wetness indicators, opacifiers, fillers, aerogels, sizing agents, antimicrobial agents, enzymes, ion exchange material, or enzyme inhibitors such as urease inhibitors to prevent the production of ammonia.

Skin comfort can be enhanced with the addition to the topsheet or body side surface of the absorbent core of other desirable materials such as aloe vera derivatives, lotions, emollients, silicone compounds, vitamin E, or derivatives of tallow and vegetable oils for softness and lubricity. Hydrophilic skin wellness agents can be advantageous, including allantoin, cationic bentonite, ascorbic acid, colloidal oatmeal, urocic acid, dex panthenol, βglucan, and the like. Agents to reduce or prevent itching and skin redness can be included on the topsheet, backsheet, or absorbent members of the present invention. Emollients and lotions in particular may be added to the body-contacting side of the wicking barrier cuff. Exemplary teachings concerning the addition of lotion to cuffs is given in PCT publication WO 98/24391-A2.

The absorbent core and particularly the absorbent material of the central absorbent member can comprise cellulosic fibers stabilized with a binder material. Likewise, the multiple layers that can be used in the outer absorbent member or the central absorbent member can be joined together with a binder material, or a binder material can attach the topsheet and/or the backsheet to the adjoining outer absorbent member or central absorbent member to improve pad integrity.

Beneath the central absorbent member, in addition to or as part of the central rising member, it is possible to add soft, resilient or gas-filled shaping elements to raise the central absorbent member into contact with a body during use. For example, conformable foam or other material may be inserted underneath the central absorbent member, either in contact with the central absorbent member or between a layer of barrier material (i.e., the wicking barrier) and the backsheet.

The absorbent articles of the present invention can also be provided with body adhesives for improved fit. Adhesives such as hydrogels can be placed on elastic cuffs or other elastic or extensible components; on flaps to make a seal against the body, as disclosed in European Patent Application 638,303-B1, "Sanitary Napkin," S. Mizutani and M. Kashiwagi, Nov. 5, 1997; on the sides, ends, or edges of articles; or in selected portions of liners or topsheets of articles.

A diaper can have a topsheet and a backsheet with length and width dimensions generally larger than those of the absorbent core. The topsheet and the backsheet extend beyond the edges of the absorbent core to thereby form the periphery of the diaper. While the topsheet, the backsheet, and the absorbent core may be assembled in a variety of well known configurations, several useful diaper configurations are described generally in U.S. Pat. No. 3,860,003 issued to Buell on Jan. 14, 1975 and U.S. Pat. No. 5,151,092 issued to Buell on Sep. 29, 1992.

Pad Stabilizers and Shaping Elements

Means can also be applied to reduce the tendency of a pad or sanitary napkin to bunch or fold over onto itself during transverse compression. Wings, flaps, or tabs extending from the absorbent article in the crotch region can fold over the edge of undergarments of the wearer to provide better fit, stability, and leakage protection, and can reduce undesirable bunching of the article. Wings and related structures are taught in the U.S. Pat. No. 5,267,992, "Shaped Sanitary Napkin with Flaps," issued to K. J. Van Tilburg, Dec. 7, 1993.; U.S. Pat. No. 4,687,478, "Shaped Sanitary Napkin with Flaps," issued to Van Tilburg, Aug. 18, 1987; U.S. Pat. No. 4,608,047, "Sanitary Napkin Attachment Means," issued to W. B. Mattingly, Aug. 26, 1986; U.S. Pat. No. 5,342,342, "Disposable Diapers," issued to Kitaoka Aug. 30, 1994; and World Patent Application 99/00093 by R. W. Patterson et al., published Jan. 7, 1999.

Apart from the use of wings and fasteners for stability and fit, preshaping of a pad can also be useful, including the means disclosed in U.S. Pat. No. 5,545,156, issued Aug. 13, 1996 to DiPalma et al. Thus, a pad can be contoured or shaped for better body fit. In one embodiment, the absorbent article is profiled so that it is thicker in the center of the article and tapers so it becomes thinner at the longitudinal sides and/or at the front and back edges. Profiling can be achieved by layering, by depositing absorbent material with a nonuniform basis weight distribution, by using profiled molds to shape the article, by selective calendering of the article, and so forth. Useful methods for imparting curvature to an absorbent article are disclosed by Olsen et al. in U.S. Pat. No. 5,591,150, issued Jan. 7, 1997.

It is also desirable to provide the absorbent core of the article with cuts, embossments, or score lines to direct the manner in which the article bends or buckles when in use such that good body fit is achieved. Examples of such an approach are disclosed in U.S. Pat. No. 5,514,104, issued May. 7, 1996 to Cole et al. Embossments in the central absorbent member are desirable to promote a fold along the longitudinal centerline in sanitary napkins. Desirably, the embossments (densified areas) should rise toward the body rather than descend away from the body to encourage the central absorbent member to fold up toward the body when compressed from the sides in use.

Methods of Making

Generally, automated equipment can be used similar to the production lines already used for production of sanitary napkins, diapers, and the like, with minor modifications to produce the present invention. Modular systems are especially preferred, wherein the various unit operations in the production line can be moved and replaced with other modules without necessitating a complete rebuild of a machine.

The production line can include a hammermill for production of comminuted fibers, if fluff pulp is to be used, or absorbent material in roll form can be provided, including airlaid webs, coform, mechanically softened pulp sheets, tissue webs, and the like. Likewise, the nonwoven or film components of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another, and may be further transported with vacuum pick up shoes, jets of air, mechanical pincers, and the like.

For example, a web of airlaid material, coform, or a microstrained pulp sheet of width suitable for the absorbent core of an absorbent article may be unwound and slit into three strips, the middle strip desirably being wider than either of the two side strips. Alternatively, strips from three rolls of absorbent material may be unwound and brought into proximity to each other. The three strips are directed in the same direction, the machine direction, with two side strips spaced apart by a width approximately equal to or less than the width of the middle strip. The middle strip is elevated relative to the side strips, being guided and positioned by guiding means such as rolls, turning bars, foils, channels, pneumatic jets, vacuum slots or shoes, or the like. A web of barrier material, such as an embossed polyethylene film, is also unwound from a roll and is guided by guiding means to be beneath the elevated middle strip and above the side strips, traveling in the same direction. Discrete segments of foam or other spacer means may be adhesively attached along two lines on the wicking barrier material. The outer portions of the barrier material are folded back upon themselves by conventional folding devices to create a two-layered section of wicking barrier material held apart by the spacer means therebetween. The combination of the three strips and the moving web of barrier material with folded wicking barrier cuffs converge into a low-pressure nip (e.g., peak pressure desirably less than about 50 kPa, more specifically less than about 8 kPa) or joining zone where the middle strip is brought approximately into the same plane as the outer strips or into contacting relationship therewith, with direct contact at least partially blocked by the presence of the wicking barrier. The middle strip may partially overlap the two outer strips, in which case the width of the central void space defined by the inner longitudinal sides of the outer strip would be less than the width of the central absorbent member. In this manner, an absorbent core is assembled having a central absorbent member, an outer absorbent member comprising two longitudinal strips, and a wicking barrier separating the central absorbent member from the outer absorbent member. (In specifying that the middle strip be elevated, it is understood throughout the body of this specification that that the same procedures could be applied upside down to create an upside down absorbent core, in which case the middle strip would be lower than the side strips.)

The three strips and the wicking barrier may then be joined to a section of backsheet material and the article may then be attached to a topsheet. Additional absorbent layers may be joined to the absorbent core.

Optionally, a central rising member such as a cut section of an "e"-folded web may be attached at periodic, spaced apart intervals to the body-side surface of the wicking barrier after it is unwound and before it is joined to the absorbent core, in which case the central rising member will be sandwiched between the wicking barrier and middle strip as the absorbent core passes through a nip or joining zone. In a less preferred embodiment, the wicking barrier could also be attached beneath the wicking barrier to its garment-side surface prior to contacting the backsheet. The absorbent core is sandwiched between a backsheet and topsheet, both of which can be provided in roll form also. Adhesive spray or beads, rotary ultrasonic or thermal bonding devices, and other joining means can be applied to joint the topsheet and backsheet to each other and to the absorbent core, if desired. The assembled article can be cut and provided with other components as needed.

A cutter cuts the absorbent core to the proper length and it is then bonded to a backsheet such as a clothlike, breathable film that has been unwound from a roll, cut to the desired shape or length, and treated with adhesive to be joined to the absorbent core. A topsheet, also unwound from a roll, is joined adhesively, thermally, or ultrasonically, for example, to the article, particularly being attached to the backsheet at the periphery of the article. The topsheet and backsheet may then be cut together to define the proper shape for the article. Wings, adhesive tape strips, mechanical fasteners, cuffs, and the like may also be added using methods known in the art.

Related embodiments can be produced by simply stamping out the region of the absorbent core in a central region to define an outer absorbent member with a void therein. Under the outer absorbent member a liquid impervious polymeric backsheet is adhesively joined. A relatively flat central rising member is placed in the void above the backsheet, and then a central absorbent member such as a mat of fluff pulp is placed over the central rising member. A topsheet is joined to the article, either by fine adhesive spray over portions of the outer absorbent member and central absorbent member, and/or by adhesive connection to the backsheet along the periphery of the article. Desirably, excess width of the meltblown barrier layer beyond the width required to line the central void will result in a band of barrier material around the central absorbent member, which may offer a visual cue (especially if the meltblown is colored) of a protective ring around the central absorbent area and serve other valuable functions. The band can form a complete ring around the central absorbent zone, or can form longitudinal bands separating the sides of the article from the central target region.

High speed, automated equipment can be used to perform the manufacture of the article. A central absorbent member surrounded on all sides by an outer absorbent member generally must be placed into a central void with precision and good registration, which can be challenging at high speeds but still feasible. However, for ease of manufacture and reduced cost, the central absorbent member is an elongated strip that extends substantially the length of the article and is bound by the outer absorbent member only along the longitudinal sides of the central absorbent member, which sides desirably are substantially straight and parallel. In this case the central absorbent member can be a continuous strip which need only be registered laterally and cut at the ends to place it properly in the central void between an outer absorbent member comprising two discrete portions. In one embodiment, the outer absorbent member and central absorbent member are cut from a single strip of absorbent material, with the central portion (the central absorbent member) being momentarily lifted during manufacture to permit insertion of a central rising member therebeneath and optionally insertion of the wicking barrier. However, the central rising member can be centered appropriately on an adhesive-coated backsheet before attachment to the absorbent members of the article, followed by addition of the topsheet, to provide an article within the scope of the present invention.

EXAMPLES

Several examples of absorbent articles were made with the materials listed in Table 1 below:

Examples 1 and 2 were made generally according to FIG. 6, with exceptions noted below, and with the materials described in Table 1 unless otherwise noted.

In Example 1, the outer absorbent member was in the shape of a dogbone-shaped ring made of fluff pulp (a fluff ring) with a basis weight of 340 gsm and a density of 0.17 g/cc. The outer absorbent member was centered on a large (about 20 cm wide by 40 cm long) sheet of rose backsheet material with adhesive uniformly sprayed on the upper surface thereof to attach the outer absorbent member thereto. The fluff ring had a length of 23 cm, a minimum width of 6.8 cm at the transverse centerline, and a maximum width of 7.5 cm at the dogbone ends. The central void was substantially oval (a "racetrack" shape, or a rectangle with rounded ends, as depicted in FIG. 6) with a length of 18.5 cm and a width of 3.9 cm.

A white 1-mil thick polyethylene wicking barrier with a contact adhesive on both sides and with dimensions substantially larger than the fluff ring (about 10.7 cm wide by 30 cm long) was centered over the fluff ring, thus lining the central void within the outer absorbent member (the fluff ring) and covering the body-side surface of the outer absorbent member.

Two strips of about 20 gsm creped bleached kraft softwood tissue about 24 cm long and 3 cm wide were placed over the wicking barrier to remove the tack from portions of the wicking barrier that would form the inner surfaces of a

TABLE 1

Basic materials used in construction of absorbent articles for the Examples.

| Component | Manufacturer | Description |
|---|---|---|
| Topsheet | | |
| Spunbond material | Kimberly-Clark Corp. | 0.6 osy polypropylene spunbond web, "Delta" version, treated with 0.3% add-on of surfactant (described below), pin apertured |
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR54 debonded softwood pulp comminuted with a hammermill |
| Densified airlaid webs | | |
| Completed web | Concert Fabrication, Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated copolyethylene sheath, 50/50 core/sheath ratio, concentric, 2.8 dpf, with T-255 fiber finish |
| Coform | Kimberly-Clark Corp. | 60% bleached kraft southern softwood, 40% polyethylene, basis weight of 135 gsm |
| Impervious wicking barrier | | |
| Polyolefin film, white | Edison Plastics Co. | A low density polyethylene, 18 gsm, opaque with added white pigment, about 1 mil |
| Backsheet | | |
| Polyolefin film | Edison Plastics Co. | A low density polyethylene, 20 gsm, rose color, 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with a 19 mm space between them |
| Release paper | Akrosil Inc. | White base sheet, one side coated with silicone release agent, other side printed | wicking barrier cuff. One edge of each tissue strip was aligned with the outer edge of the wicking barrier. The other edge of each tissue strip was then substantially aligned with the inner edge of the fluff ring. Thus, the wicking barrier was rendered nontacky by the presence of a 3-cm wide tissue strip substantially extending from the inner edge of the fluff ring (the wall of the central void) to the outward edge of the wicking barrier, and extending over the length of the fluff ring.

A pledget of fluff pulp was then placed on the wicking barrier, centered over the central void in the fluff ring. The pledget contacted the exposed adhesive on the upper surface of the wicking barrier. The pledget comprised a 650 gsm section of fluff pulp at a density of 0.14 g/cc cut to a rounded rectangular shape about 8.5 cm long and 3.5 cm wide. An airlaid upper absorbent layer was then placed over the pledget, completely covering the central void in the fluff ring and centered over the fluff ring. The airlaid upper absorbent layer was a rounded rectangle section with a length of 20 cm and a width of 5.4 cm, a basis weight of 175 gsm, and a density of 0.08 g/cc. The airlaid upper absorbent layer was cut with a die, as was the fluff ring and the pledget.

The detackified portion of the wicking barrier (i.e., the region covered with tissue) on each side of the wicking barrier was then folded in half along a longitudinal fold passing substantially through the longitudinal centerline of each tissue strip, thus folding each tissue-covered section upon itself to bring two tissue-covered surfaces of the wicking barrier together to define a longitudinal wicking barrier cuff on each side of the absorbent article.

A topsheet with the adhesive side down was then placed over the article, completely covering the absorbent article and adhesively joining the topsheet to the upper layer of each wicking barrier cuff and to the exposed upper surface of the airlaid upper absorbent layer (substantially the portion over the central void in the fluff ring). The topsheet adhesively joined the backsheet outside of the fluff ring. The article was then die cut with a dogbone-shaped die centered over the fluff ring and having dimensions slightly larger than the fluff ring. After cutting, the rose backsheet and the topsheet had a length of 23.7 cm and a minimum width of 7.6 cm and a maximum width of 8.6 cm at the dogbone ends.

Example 1 was provided with garment adhesive and a release layer on the garment side of the backsheet.

Example 2 was made according to Example 1 except that the fluff ring was a rounded rectangle, not a dogbone shape, made from two layers of coform (2 layers at 153 gsm each for a total coform basis weight of 270 gsm). It had a length of 21.7 cm and a width of 6.1 cm. The central void therein was also a rounded rectangle and had a width of 3.6 cm and a length of 18.5 cm. The white wicking barrier film was cut to a width of 9 cm and placed over the coform ring. In this case, the wicking barrier was white polyethylene film, 1 mil, without adhesive except along a central strip 4.5 cm wide but not in the cuffs region, so no detackifying means was required to prevent adhesive contact between the two internal surfaces of the wicking barrier cuff. The pledget placed over the wicking barrier lining in the central void was 3.1 cm wide and 8.5 cm long, in a rounded rectangle shape. Over the pledget was placed the upper absorbent layer in the form of an airlaid strip with a basis weight of 175 gsm and a density of 0.08 g/cc, cut to a length of 194 mm and a width of 48 mm. After the pledget and airlaid upper absorbent layer were in place, the outer portion of the wicking barrier extending transversely beyond the edge of the fluff ring was folded back upon itself toward the longitudinal, defining an upper layer of a wicking barrier with a width of about 1.5 cm. The upper layer of the wicking barrier cuff extended inwardly sufficiently far to contact the body-side surface of the airlaid upper absorbent layer. A nonwoven topsheet was then placed over the article, as before, and the article was cut to the same dogbone shape as in Example 1. In Example 2, the wicking barrier cuff is held open by adhesive contact of the upper layer of the wicking barrier cuff with the topsheet and by the presence of the longitudinal sides of the upper absorbent layer between the upper side and lower side of the wicking barrier cuff.

In Example 2, slight lateral compression of the absorbent article from the longitudinal sides results in upward deflection of the wicking barrier cuff and the attached portion of the topsheet, forming a longitudinal dynamic bubble cuff that can contact the body.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article for use on the body of a wearer, the absorbent article having two longitudinal sides, a target zone and a body side, the absorbent article comprising:
   a) a liquid impervious backsheet;
   b) a liquid pervious topsheet attached to the backsheet;
   c) an absorbent core positioned between the topsheet and the backsheet, the absorbent core comprising an outer absorbent member and a central absorbent member, the outer absorbent member having a width in the target zone greater than the width of the central absorbent member in the target zone; and
   d) a wicking barrier at least in part separating the central absorbent member from the outer absorbent member, the wicking barrier passing beneath the central absorbent member and having a vertical component extending vertically from beneath the central absorbent member to a surface of the outer absorbent member, further comprising a folded-over portion above the absorbent core forming a wicking barrier cuff open toward the central absorbent member.

2. The absorbent article of claim 1, further comprising a central rising member.

3. The absorbent article of claim 1, further comprising absorbent material which expands vertically when wetted, selected from regenerated cellulose, calendered tissue webs, densified flash-dried fibers, or creped tissue connected to a stability layer.

4. The absorbent article of claim 1, the wicking barrier cuff further comprising spacer means to hold the cuff open to receive fluid.

5. The absorbent article of claim 1, wherein the central absorbent member overlaps a portion of the outer absorbent member.

6. The absorbent article of claim 1, wherein the central absorbent member is substantially unattached to the outer absorbent member in the target zone.

7. The absorbent article of claim 1, wherein the outer absorbent member has a thickness and the central absorbent member comprises a lower layer having a thickness and a width, the thickness being greater than the thickness of the outer absorbent member and further comprises an upper layer having a width greater than the width of the lower layer.

8. The absorbent article of claim 1,
wherein the outer absorbent member is divided longitudinally into two discontiguous sections.

9. The absorbent article of claim 1,
wherein the outer absorbent member comprises a central void extending partially through the outer absorbent member.

10. The absorbent article of claim 1,
wherein a central void passes completely through the outer absorbent member.

11. The absorbent article of claim 1,
wherein the central absorbent member further comprises a central porthole opening.

12. The absorbent article of claim 1, wherein the central absorbent member further comprises cellulosic materials which swell substantially in the vertical direction upon wetting.

13. The absorbent article of claim 1,
wherein the wicking barrier is selected from an apertured film, a polymeric film having at least one aperture, a hydrophobic nonwoven web, a fibrous web comprising sizing agents, and a tissue layer comprising hydrophobic material.

14. The absorbent article of claim 1,
wherein the wicking barrier comprises a substantially impervious film.

15. The absorbent article of claim 1, wherein the absorbent article is extensible.

16. The absorbent article of claim 1,
wherein the wicking barrier consists essentially of a non-absorbent material.

17. An absorbent article having a longitudinal direction, a transverse direction, a vertical direction substantially normal to both the longitudinal and transverse directions, and a body side, comprising:
a) a fluid pervious topsheet on the body side of the article;
b) a backsheet connected to the topsheet;
c) an absorbent core having a body side surface, the core being disposed between the backsheet and the topsheet, the core comprising an outer absorbent member having a central void open toward the body side of the article, and a central absorbent member disposed over the central void of the outer absorbent member and extending into the void; and
d) a wicking barrier disposed between the outer absorbent member and the central absorbent member, the wicking barrier passing beneath the central absorbent member and having a vertical component extending vertically from beneath the central absorbent member to a surface of the outer absorbent member, and a wicking barrier cuff on the body side surface of the absorbent core.

18. The absorbent article of claim 17, the wicking barrier cuff further comprising spacer means to hold the cuff open to receive fluid.

19. The absorbent article of claim 17, wherein the central absorbent member overlaps a portion of the outer absorbent member.

20. The absorbent article of claim 17, wherein the central absorbent member is substantially unattached to the outer absorbent member in the target zone.

21. The absorbent article of claim 17, wherein the outer absorbent member has a thickness and the central absorbent member comprises a lower layer having a thickness and a width, the thickness being greater than the thickness of the outer absorbent member and further comprises an upper layer having a width greater than the width of the lower layer.

22. The absorbent article of claim 17, wherein the outer absorbent member is divided longitudinally into two discontiguous sections.

23. The absorbent article of claim 17, wherein the outer absorbent member comprises a central void extending partially through the outer absorbent member.

24. The absorbent article of claim 17, wherein a central void passes completely through the outer absorbent member.

25. The absorbent article of claim 17, wherein the central absorbent member further comprises a central port-hole opening.

26. The absorbent article of claim 17, wherein the wicking barrier consists essentially of a non-absorbent material.

27. An absorbent article for use on the body of a wearer, the absorbent article having two longitudinal sides, a target zone and a body article comprising:
a) a liquid impervious backsheet;
b) a liquid pervious topsheet attached to the backsheet;
c) an absorbent core positioned between the topsheet and the backsheet, the absorbent core comprising a central portion and an outer portion; and
d) a wicking barrier at least in part separating the central portion from the outer portion, the wicking barrier passing beneath the central portion and having a vertical component extending vertically from beneath the central portion to a surface of the outer portion, further extending laterally outward from the central portion toward a longitudinal side of the article to span a first horizontal distance, whereupon the wicking barrier folds back upon itself toward the longitudinal centerline, spanning a second horizontal distance and forming a wicking barrier cuff with an upper layer and a lower layer, the cuff being open toward the central absorbent member and closed toward the longitudinal sides of the article.

28. The article of claim 27, further comprising spacer means to hold open spaces between the upper layer and lower layer of the wicking barrier cuff.

29. The article of claim 28, wherein the spacer means comprises a material which swells substantially upon wetting.

30. An absorbent article for use on the body of a wearer, the absorbent article having two longitudinal sides, a longitudinal centerline, a target zone and a body side, the absorbent article comprising:
a) a backsheet;
b) a liquid pervious topsheet attached to the backsheet;
c) a central absorbent member positioned between the topsheet and the backsheet, the central absorbent member comprising longitudinal sides and a body-side surface;
d) a liquid impervious wicking barrier that extends beneath the central absorbent member, wraps the longitudinal sides thereof, and thereupon extends a horizontal distance on the body-side surface thereof toward the longitudinal centerline of the absorbent article; and e) spacer means to provide void space between the central absorbent member and the portion of the wicking barrier above the body-side surface of the central absorbent member, thereby forming a wicking barrier cuff.

31. The absorbent article of claim 30, wherein the spacer means are selected from segments of foam, a cellulosic web, or elastic spacers.

32. The absorbent article of claim 30, wherein the spacer means comprise attachment to a topsheet which holds the wicking barrier open.

33. The absorbent article of claim 30, wherein the spacer means comprise segments of deformable matter spaced longitudinally apart to provide open spaces therebetween.

34. The absorbent article of claim 30, wherein the spacer means comprise strips of deformable matter having a plurality of openings therein for receiving fluid.

35. The article of claim 30, wherein the spacer means comprises a material which swells substantially upon wetting.

36. The absorbent article of claim 30, wherein the spacer means separate the upper layer of the wicking barrier from the lower layer of the wicking barrier by at least 0.2 mm.

37. The absorbent article of claim 3, wherein the spacer means separate the upper layer of the wicking barrier from the lower layer of the wicking barrier by about 1 mm or greater.

38. The absorbent article of claim 30, wherein the spacer means separate the upper layer of the wicking barrier from body-side surface of the absorbent member to provide a plurality of openings for receiving fluid in the wicking barrier cuff, the openings having a height of about 0.5 mm or greater.

39. The absorbent article of claim 30,
wherein the wicking barrier is selected from a hydrophobic nonwoven web, a fibrous web comprising sizing agents, and a tissue layer comprising hydrophobic material.

40. The absorbent article of claim 30,
wherein the wicking barrier comprises a substantially impervious film.

41. The absorbent article of claim 30, wherein the absorbent article is extensible.

42. The absorbent article of claim 30,
wherein the wicking barrier consists essentially of a non-absorbent material.

43. An absorbent article for use on the body of a wearer, the absorbent article having two longitudinal sides, a longitudinal centerline, a target zone and a body side, the absorbent article comprising:
 a) a backsheet;
 b) a liquid pervious topsheet attached to the backsheet;
 c) a central absorbent member positioned between the topsheet and the backsheet, the central absorbent member comprising longitudinal sides and a body-side surface;
 d) a wicking barrier that extends beneath the central absorbent member, wraps the longitudinal sides thereof, and thereupon extends a horizontal distance on the body-side surface thereof toward the longitudinal centerline of the absorbent article; and
 e) spacer means to provide void space between the central absorbent member and the portion of the wicking barrier above the body-side surface of the central absorbent member, thereby forming a wicking barrier cuff, wherein the spacer means comprise corrugations or embossments in the wicking barrier.

44. An absorbent article for use on the body of a wearer, the absorbent article having two longitudinal sides, a target zone, a body side, and a longitudinal centerline, the absorbent article comprising:
 a) a backsheet;
 b) a liquid pervious topsheet attached to the backsheet;
 c) an absorbent core positioned between the topsheet and the backsheet, the absorbent core comprising longitudinal sides, a body-side surface, a lower absorbent layer having a width, and an upper absorbent layer having a width substantially less than the width of the lower absorbent layer; and
 d) a liquid impervious wicking barrier extending along a portion of the body-side surface of the lower absorbent layer in the target region and further being folded about a substantially longitudinal folding line toward the longitudinal centerline of the absorbent article to form a wicking barrier cuff having an upper layer and a lower layer, the upper layer being attached to the topsheet, and the folding line being transversely away from the upper absorbent layer.

45. The absorbent article of claim 44, wherein the upper layer of the wicking barrier contacts the body-side surface of the upper absorbent layer of the absorbent core.

46. The absorbent article of claim 44, further comprising spacer means to hold the wicking barrier cuff open.

47. The absorbent article of claim 44, wherein a portion of the topsheet is attached to an upper layer of the wicking barrier cuff and wherein lateral compression in the target region causes the portion of the topsheet attached to the upper layer of the wicking barrier cuff to deflect upwards, forming a dynamic bubble cuff capable of receiving fluid flowing transversely outward from the center of the article.

48. The absorbent article of claim 44, wherein the wicking barrier is non-absorbent.

49. An absorbent article for use on the body of a wearer, the absorbent article having two longitudinal sides, a target zone and a body side, the absorbent article comprising:
 a) a liquid impervious backsheet;
 b) a liquid pervious topsheet attached to the backsheet;
 c) an absorbent core positioned between the topsheet and the backsheet, the absorbent core comprising an outer absorbent member and a central absorbent member, the outer absorbent member having a width in the target zone greater than the width of the central absorbent member in the target zone; and
 d) a wicking barrier passing beneath the central absorbent member and having a vertical component extending vertically from beneath the central absorbent member to a surface of the outer absorbent member, further comprising a folded-over portion above the absorbent core forming a wicking barrier cuff open toward the central absorbent member,
 wherein a portion of the topsheet is attached to an upper layer of the wicking barrier cuff and wherein lateral compression in the target region causes the portion of the topsheet attached to the upper layer of the wicking barrier cuff to deflect upwards, forming a dynamic bubble cuff capable of receiving fluid flowing transversely outward from the center of the article.

50. A method for producing an absorbent article having a longitudinal centerline, the method comprising:
 a) preparing a lower layer of absorbent material having a width;
 b) disposing a wicking barrier over the lower layer of absorbent material, the wicking barrier having a width substantially greater than the width of the lower layer of absorbent material;

c) disposing an upper absorbent layer over the wicking barrier, the upper absorbent layer having a width less than the width of the outer absorbent member;

d) folding the transversely outer portions of the wicking barrier back toward the longitudinal centerline of the article to form wicking barrier cuffs each comprising a lower layer and an upper layer, the upper layer having a free end toward the longitudinal centerline of the article;

e) disposing a backsheet beneath the lower layer of absorbent material; and f) disposing a topsheet over the article and attaching the topsheet to the backsheet.

51. The method of claim 50, further comprising providing spacer means in the wicking barrier cuff.

52. A method for producing an absorbent article having a central absorbent member, a garment side, a body side, and a longitudinal centerline, the method comprising:

a) providing a central strip of absorbent material and two side strips of absorbent material to form an incipient absorbent core;

b) placing a thin, flexible wicking barrier below the central strip and above the two side strips, the wicking barrier having a width substantial greater than the width of the central strip and having a vertical component extending vertically from beneath the central strip to a surface of the two side strips;

c) upwardly folding the transversely outer portions of the wicking barrier back upon themselves and toward the longitudinal centerline of the central strip to form wicking barrier cuffs;

d) disposing a backsheet beneath the central strip and two side strips, the backsheet having larger in-plane dimensions that the combined central strip and two side strips; and e) disposing a topsheet over the central absorbent strip and two side strips, wherein the topsheet is further connected to the backsheet at the outer periphery thereof.

53. The method of claim 52, further comprising inserting a pledget of absorbent article between the wicking barrier and the central absorbent strip.

54. The method of claim 52, further comprising providing spacer means in the wicking barrier cuff.

\* \* \* \* \*